(12) United States Patent
Schuler

(10) Patent No.: US 9,492,478 B2
(45) Date of Patent: *Nov. 15, 2016

(54) ENCODED BIOELECTRONIC METHOD AND SYSTEM AND CALCIUM TREATMENT FOR SLAYING CANCER BY RAPID TRIGGERING OF CELLULAR APOPTOSIS AND KARYORRHEXIS

(71) Applicant: Neuro Code Tech Holdings, LLC, Albuquerque, NM (US)

(72) Inventor: Eleanor L. Schuler, Rio Rancho, NM (US)

(73) Assignee: Neuro Code Tech Holdings, LLC, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/046,866

(22) Filed: Feb. 18, 2016

(65) Prior Publication Data

US 2016/0235783 A1    Aug. 18, 2016

Related U.S. Application Data

(63) Continuation of application No. 14/621,659, filed on Feb. 13, 2015, now Pat. No. 9,295,835.

(60) Provisional application No. 61/940,054, filed on Feb. 14, 2014.

(51) Int. Cl.
*A61K 33/06* (2006.01)
*A61N 1/30* (2006.01)
(Continued)

(52) U.S. Cl.
CPC .............. *A61K 33/06* (2013.01); *A61K 41/00* (2013.01); *A61K 41/0004* (2013.01); *A61N 1/205* (2013.01); *A61N 1/30* (2013.01); *A61N 1/32* (2013.01); *B82Y 30/00* (2013.01)

(58) Field of Classification Search
CPC .......... A61K 41/00; A51K 33/06; A61N 1/30
See application file for complete search history.

(56) References Cited

U.S. PATENT DOCUMENTS 8,315,712 B2 * 11/2012 Schuler .................. A61N 1/205
607/2
8,656,930 B2    2/2014 Schuler et al.
(Continued)

FOREIGN PATENT DOCUMENTS

WO    2009151783 A1    12/2009

OTHER PUBLICATIONS

U.S. Appl. No. 12/334,212, filed Dec. 12, 2008, Schuler et al.
(Continued)

*Primary Examiner* — Catherine Voorhees
(74) *Attorney, Agent, or Firm* — Kermit D. Lopez; Luis M. Ortiz; Ortiz & Lopez, PLLC

(57) ABSTRACT

A bioelectronic medical method and system for rapidly destroying living cancer cells and the tumors they create including metastatic off-spring of such tumor(s) regardless of their location within a human or animal body. Calcium ions can be inserted into a nucleus of a cancer cell(s). The nucleus of the cancer cell(s) is then fragmented among many cancer cells (e.g., in a tumor) simultaneously with the transmission of a destructive analog electrically encoded signals to provide a medical cancer treatment thereof. A first target of medical cancer treatment is aimed principally into the nucleus and mitochondrion bodies of a malignancy associated with the cancer cell(s).

20 Claims, 9 Drawing Sheets

(51) Int. Cl.
    *A61K 41/00*     (2006.01)
    *A61N 1/20*     (2006.01)
    *A61N 1/32*     (2006.01)
    *B82Y 30/00*     (2011.01)

(56) References Cited

U.S. PATENT DOCUMENTS

| | | | |
|---|---|---|---|
| 8,831,738 B2 * | 9/2014 | Schuler | A61N 1/32 607/2 |
| 9,032,964 B2 | 5/2015 | Schuler et al. | |
| 9,295,835 B2 * | 3/2016 | Schuler | A61K 33/06 |
| 2005/0222646 A1 | 10/2005 | Kroll et al. | |
| 2006/0084942 A1 | 4/2006 | Kim et al. | |
| 2006/0093646 A1 | 5/2006 | Cima et al. | |
| 2010/0286689 A1 | 11/2010 | Schuler et al. | |
| 2011/0130754 A1 | 6/2011 | Schuler et al. | |
| 2011/0270248 A1 | 11/2011 | Schuler et al. | |
| 2014/0228910 A1 | 8/2014 | Schuler et al. | |
| 2015/0065946 A1 * | 3/2015 | Gehl | A61K 31/7064 604/22 |
| 2015/0231243 A1 | 8/2015 | Schuler | |
| 2015/0258318 A1 | 9/2015 | Schuler | |
| 2015/0313537 A1 | 11/2015 | Schuler | |

OTHER PUBLICATIONS

U.S. Appl. No. 14/182,417, filed Feb. 18, 2014, Schuler et al.
U.S. Appl. No. 14/621,659, filed Feb. 13, 2015, Schuler.
Davalos, R. V. et al., Tissue Ablation with Irreversible Electroporation, Annals of Biomedical Engineering (2005) 33 (2):223-231.
Farboud, B. et al., DC Electric Fields Induce Rapid Directional Migration in Cultured Human Corneal Epithelial Cells, Exp. Eye Res. (2000) 70:667-673.
Hu, Q. et al., Simulations of transient membrane behavior in cells subjected to a high-intensity ultrashort electric pulse, Physical Review E (2005) 71, 031914, 9 pages.
Nagayo, T. et al., Cancer cell biology (1981) Scientific Societies Press, Tokyo, Japan (book).
Famm, K., A jump-start for electroceuticals, Nature Apr. 11, 2013, 496:159-161.
Nuccitelli, R. et al., Nanosecond pulsed electric fields cause melanomas to self-destruct, Biochemical and Biophysical Research Communications (2006) 343:351-360.
Response to Office Action dated Mar. 23, 2011—U.S. Appl. No. 12/334,212.
Office Action, Sep. 23, 2011—U.S. Appl. No. 12/334,212.
Office Action, Jan. 31, 2012—U.S. Appl. No. 12/334,212.
Response to Office Action of Jan. 31, 2012—U.S. Appl. No. 12/334,212.
Office Action—Mar. 26, 2012—U.S. Appl. No. 12/334,212.
Declaration of Eleanor Schuler, Signed Jun. 20, 2012—U.S. Appl. No. 12/334,212.
Response to Office Action of Mar. 26, 2012—U.S. Appl. No. 12/334,212.
Office Action—Jul. 18, 2012—U.S. Appl. No. 12/334,212.
Office Action—Jan. 4, 2013—U.S. Appl. No. 12/334,212.
Appeal Brief, Nov. 27, 2013—U.S. Appl. No. 12/334,212.
Examiner's Answer, Jan. 21, 2014—U.S. Appl. No. 12/334,212.
Reply Brief, Mar. 21, 2014—U.S. Appl. No. 12/334,212.
Decision on Appeal, Jun. 7, 2016—U.S. Appl. No. 12/334,212.

* cited by examiner

ENCODED BIOELECTRONIC METHOD AND SYSTEM AND CALCIUM TREATMENT FOR SLAYING CANCER BY RAPID TRIGGERING OF CELLULAR APOPTOSIS AND KARYORRHEXIS

CROSS-REFERENCE TO PATENT APPLICATION

This application is a continuation of U.S. patent application Ser. No. 14/621,659, entitled "Encoded Bioelectronic Method and System and Calcium Treatment for Slaying Cancer by Rapid Triggering of Cellular Apoptosis and Karyorrhexis," which was filed on Feb. 13, 2015, and which claims priority under 35 U.S.C. 119(e) to U.S. Provisional Patent Application Ser. No. 61/940,054, entitled "Encoded Bioelectronic Method and System and Calcium Treatment for Slaying Cancer by Rapid Triggering of Cellular Apoptosis and Karyorrhexis," which was filed on Feb. 14, 2014, the disclosures of which are respectively incorporated herein by reference in their entirety.

TECHNICAL FIELD

Embodiments relates generally relate to the field of bioelectronic medicine. Embodiments further relate to the alteration of cancer cell internal electrical signals so as to trigger and induce cell death. Embodiments additionally relate to inducing apoptosis (programmed cell death) in cancer cells due to reprogramming the intra-cellular operational communication network. Embodiments also relate to the use of calcium and related compounds and processes for use in damaging and destroying cancer cells.

BACKGROUND OF THE INVENTION

The fact that Tony Snow died at age 53 of colon cancer is a lesson to everyone. Once cancer appears, your health and life span are in jeopardy. Tony had access to the National Cancer Institute (NCI) because of his closeness, as press spokesman for U.S. President George W. Bush and also having Georgetown University standing by to help with treatment technologies. Tony's mother died from the same genetic cancer and despite his own repeated diagnostic testing and aggressive treatments he was unable to defeat the malignant disease. When his colon cancer spread aggressively to his liver that sealed his fate, and death became certain. Present-day cancer treatment therapy is only an effort—not a guarantee. Tony's death is just one example, which demonstrates that cancer effects everyone—the rich, powerful and otherwise.

The World Health Organization (WHO) is a division of the United Nations that issued a press release on Feb. 5, 2014, reporting that the cost globally of cancer was estimated at $1.16 trillion in 2010. The international Agency for Research on Cancer, the specialized cancer agency of WHO has reported that new cancer cases will skyrocket globally from an estimated 14 million in 2012 to 22 million new cases a year within the next two decades. The burden internationally has doubled over the last 20 year, and it will double over the next 20.

The number of cancer deaths in the USA has risen as the population has grown, from 400,000 in 1990 to 550,000 in 2013.

The embodiments described herein moves the main technology for treating cancer away from chemotherapy, which affects the entire body, and toward the use of tiny electrical neuro encoded signals with calcium as an aimed treatment for solid tumors both within or on the surface of the human or animal body.

Early Neuro-Electric History

In 1780, Luigi Galvani, an Italian anatomist, attached two dissimilar wires to the spine of a large decapitated frog. Galvani passed a current into the frog by means of a static-electrically-charge rod and made the animal's legs jerk. He determined that nerves conducted electricity and at that moment launched the science of neurophysiology. Galvani's friend, Alessandro Volta, the inventor of the wet-cell battery, commented in 1800 that it was the electrical stimulation from the bi-metal wires, which provided the energy to make the frog's legs kick. Thus began the use of stimulating currents to induce neurons to fire their signals, which continues in research universities to this very day.

It never occurred to anyone in those early years, however, that the nerves were actually capable of generating signals on their own without the requirement for some sort of electrical stimulation. It is important to realized that there was no possible way to visualize the cells until after the microscope was invented by Zacharias Jansen in 1590. It was not until the 1600's that Antony van Leeuwenhoek improved upon that invention and was able to peer at what he referred to as "animalcules." What Leeuwenhoek saw were microbes, which was previously unrealized by anyone. He mentioned that there had to be some connection between what he saw and diseases. Early microscopes were not used to study cellular or nervous system structure.

The microscope became more prevalent throughout most university laboratories by 1830 when many biologists began to explore the makeup of life. In Berlin around 1840, Theodor Schwann and Jacob Schleiden, established that discrete cells were indeed the architectural building blocks of living tissue, be they plant or animal. This discovery paved the way for others to think about the individual function of many different kinds of cells. Previously, in 1836, Jan Purkinje, a Czech histology and physiologist and his student Gabriel Valentine were able to claim that "the entire nervous system is made up of globules (cells) and continuous primitive fibers (axons)." In 1837, Purkinje was able to describe brain cells with their nuclei and dendrites and the flask-like cells named "Purkinje cells," which are efferent types.

By 1870, very few scientists knew what a neuron really was, much less what it looked like, or how it worked. Therefore, it was still impossible to describe a three-dimensional nervous system at that time in history. But this was to change around 1877 when Camillo Golgi of Italy was able to silver-stain individual neurons so they could be studied under the microscope. Using Golgi's stain, a Spanish professor was able to begin an exhaustive study of the details of neuronal anatomy. Santiago Ramon y Cajal had proposed that neurons were the signaling units for the entire nervous system. This is often referred to as the beginning of the "neuron doctrine." From 1879, Cajal exhaustively studied the brain and many of its structures as he enlarged his understanding of the nervous system. Cajal published numerous technical papers to begin his explanation of the anatomical structure of nerves and the brain. Cajal became recognized throughout Europe by 1889 for his important work. As a result, both Golgi and Cajal shared the Nobel prized in physiology and medicine in 1906.

It was not until the late $20^{th}$ and early $21^{st}$ centuries that true bioelectronic medical treatment approaches involving the use of neuro-coded or electrical signaling technologies were possible. Recent advances in technology have allowed for the development of bioelectronic approaches to treating a variety of conditions, including cancer. True bioelectronic medical treatment applications are now possible given advancements in electronics and a better understand of how conditions such as cancer actually function in the human body.

The present inventor has been involved in the development of the premier bioelectronic technology of our time as outlined in a variety of bioelectronic medical treatment patents and patent applications covering the use of neuro-coded signaling technology. Validation of this bioelectronic technology is evidence by the fact that large pharmaceutical companies and organizations are now moving into the field of bioelectronics, albeit many years after the present inventors initial patent application filings and without much in the way of intellectual property. For example, the monolithic international pharmaceutical giant GSK (GlaxoSmithKline) announced in 2013 that it was pursuing an effort toward the development of "electroceutical" or bioelectronic medicine (see "A Jumpstart-Start for Electroceuticals, Nature", 11 Apr. 2013, Vol 496, pp. 159-161, Famm et al). Ironically, the present inventor's own research and thinking in the bioelectronic area was captured in patent filings many years prior to GSK's 2013 initiative.

To date, the primary approach to treating cancer based on bioelectronic technology has been outlined in patents and patent application publications by the present inventor. Such inventions are disclosed in, for example, U.S. Patent Application Publication No. 2010/0286689 entitled "Method and System for Processing Cancer Cell Electrical Signals for Medical Therapy," which published on Nov. 11, 2010; U.S. Patent Application Publication No. 2011/0270248 entitled "System and Method to Elicit Apoptosis in Malignant Tumor Cells for Medical Treatment," which published on Nov. 3, 2011; U.S. Patent Application Publication No. 2011/0130754 entitled "Hybrid Scientific Computer System for Processing Cancer Cell Signals as Medical Therapy," which published on Jun. 2, 2011; and U.S. patent application Ser. No. 12/334,212 entitled "Method to Switch-Off Cancer Cell Electrical Communication Codes as Medical Therapy," which was filed on Dec. 12, 2008. U.S. Patent Application Publication Nos. 2010/0286689; 2011/0270248; and 2011/0130754; and U.S. patent application Ser. No. 12/334,212 are incorporated herein by reference in their entireties.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for an improved cancer treatment technology.

It is another aspect of the disclosed embodiments to provide for methods and systems for the alteration of cancer cell internal electrical signals so as to trigger and induce cell death.

It is yet another aspect of the disclosed embodiments to provide methods and systems for inducing or eliciting apoptosis (programmed cell death) in cancer cells due to reprogramming the intra-cellular operational communication network.

It is still another aspect of the disclosed embodiments to trigger Karyorrhexis in cancer cells.

It is a further aspect of the disclosed embodiments to trigger apoptosis and Karyorrhexis in cancer cells.

It is also an aspect of the disclosed embodiments to provide methods and systems for using calcium and related compounds and processes for damaging and destroying cancer cells in association with the disclosed bioelectronic medical treatment(s).

The aforementioned aspects and other objectives and advantages can now be achieved as described herein. Bioelectronic medical methods and systems are disclosed herein for rapidly destroying living cancer cells and the tumors they create including metastatic off-spring of such tumor(s) regardless of their location within a human or animal body. Calcium ions can be inserted into a nucleus of a cancer cell(s). The nucleus of the cancer cell(s) is then fragmented among many cancer cells (e.g., in a tumor) simultaneously with the transmission of a destructive analog electrically encoded signals to provide a medical cancer treatment thereof. A first target of medical cancer treatment is aimed principally into the nucleus and mitochondrion bodies of a malignancy associated with the cancer cell(s).

Computer generated analog treatment signal(s), which are aimed at the cellular nucleus, are transmitted through the plasma membrane or its ion channel pathways. Signals travel directly through the phosphor-lipid bi-layer and through the internal membrane surface so as to enter the cellular interior. The treatment signals may travel on the intermediate and or microfilaments located in the cancer cellular interior to reach the nucleus.

The treatment signal(s) reach and influence the nucleus and are expected to participate in causing apoptosis and/or Karyorrhexis, which leads to the fragmentation and destruction of such nucleus as an operating organelle of the cancer cell. A fractured nucleus thus leads to rapid death of the cancer cell, which will be unable to reproduce or communicate with its neighboring cells within the tumor proper.

As part of the cancer destruction process, calcium can be injected into the process with the nucleus and also to influence the energy source of the cell. That energy source is an organelle that floats around in the cytoplasm called a mitochondrion.

The calcium influences the operational pace of mitochondrion output by converting adenosine diphosphate (ADP) in a resynthesizing process as adenosine tri-phosphate (ATP). ATP is a kind of bio-fuel for the cell. In operation as a cellular fuel to free up chemical energy which is transferred from ATP to provide the chemical source required for anabolic reactions for cellular processes as it reverts itself back to ADP.

A number of embodiments are disclosed herein, preferred and alternative. For example, in one embodiment, a method for destroying cancer cells, can be implemented and can include, for example, the steps or logical operations of inserting calcium ions into a nucleus of at least one cancer cell among a plurality of cancer cells; and fragmenting the nucleus in many cancer cells among the plurality of cancer cells simultaneously with the transmission of destructive analog electrically encoded signals to provide a medical cancer treatment thereof. In another embodiment, a first target of medical cancer treatment is aimed principally into the nucleus and mitochondrion bodies of a malignancy associated with the at least one cancer cell.

In another embodiment, a step or logical operation can be implemented for simultaneously treating thousands or millions of nuclei and mitochondrion cells among the plurality of cancer cells with calcium and neuro encoded analog signals to cause rapid killing of a tumor associated with the malignancy and/or the plurality of cancer cells. In yet another embodiment, an encoded electrical signal burst can be utilized on each malignant solid tumor associated with the at least one cancer cell, regardless of it being within the body or on the surface of a patient thereof, as a part of the medical cancer treatment.

In still another embodiment, a step or logical operation can be implemented for injecting the calcium into, painting the calcium on, pasting the calcium on, and/or spraying the calcium onto a surface of the plurality of cancer cells operating within a tumor, so that the calcium boosts cellular resident operating signals associated with the plurality of cancer cells above their natural electrical excitability and/or metabolic pace throughout. In still another embodiment emplacement of calcium C++ both inside a tumor associated with the at least one cancer cell and on an outer plasma membrane of the at least one cancer cell can be conducted simultaneously. In yet another embodiment, a step or logical operation can be provided for over-wrapping a tumor associated the at least one cancer cell among the plurality of cancer cells with a waterproof material if the tumor is situated in a location accessible to the over-wrapping. In still another embodiment, a step or logical operation can be provided for maintaining the waterproof material on the tumor for a particular period of time or such time as a physician deems appropriate.

In yet another embodiment, a step or logical operation can be provided for smothering a tumor associated with the at least one cancer cell from a calcium saturated wrap to deny access to extra cellular solute concentration around the at least one cancer cell or the tumor associated with the at least one cancer cell to inhibit a transport of solutes and ions and water to cause the at least one cancer cell to suffer osmotic shock causing swelling and either to burst or undergo apoptosis. In still another embodiment, a high-speed hybrid system can be employed to record from varying types of electrodes, signals associated with the at least one cancer cell to process the signals to produce the destructive analog electrically encoded signals. In another embodiment, one or more electrodes among the varying types of electrodes can be capable of piercing a plasma membrane associated with the at least one cancer cell. In yet another embodiment, at least one electrode among the varying types of electrodes can be provided as, for example, a pipette electrode or a patch-clamp hollow glass electrode with saline solution electrodes so as to enter calcium, potassium or sodium ion ports of the at least one cancer cell to record the signals associated with the at least one cancer cell.

In another embodiment, a system for destroying cancer cells, can be implemented. Such a system can include, for example, a processor and/or a memory; a device for inserting calcium ions into a nucleus of at least one cancer cell among a plurality of cancer cells; and wherein the nucleus is fragmented in many cancer cells among the plurality of cancer cells simultaneously with the transmission of destructive analog electrically encoded signals processed by the processor and/or retrieved from the memory to provide a medical cancer treatment thereof.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the principles of the present invention.

DETAILED DESCRIPTION

Figure 1:
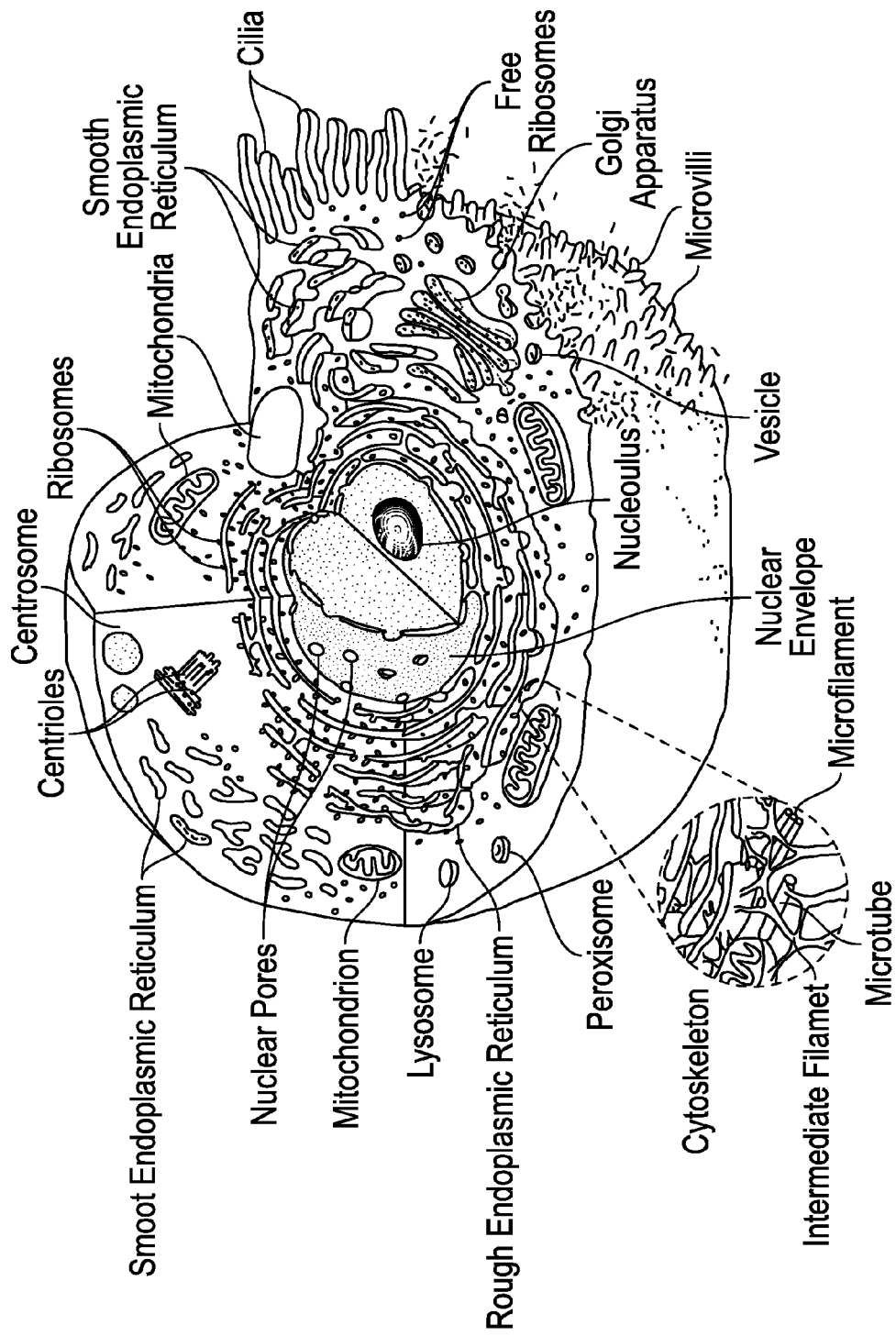
FIG. 1 illustrate a pictorial drawing of cell components.

The particular values and configurations discussed in these non-limiting examples can be varied and are cited merely to illustrate at least one embodiment and are not intended to limit the scope thereof.

The disclosed embodiments generally cover the alteration of cancer cell internal electrical signals so as to trigger and induce cell death. A primary mechanism of such embodiments relates to inducing apoptosis (programmed cell death) in cancer cells due to reprogramming the intra-cellular operational communication network. Although it might be thought that many cancer cells are not susceptible or capable of undertaking a programmed cell death because of the immortal nature of healthy cancer cells, which just keep on reproducing. The embodiments, however, provide a technological approach to altering the protective negative charge of the cancerous glycocalyx to a positive charge to induce the nucleus into taking-in and accepting the apoptosis command signals, which are aimed at shutting-down the cellular operations in an apoptosis death-spiral leading to apoptosis.

Cancer plasma membrane electrical shielding protections go from negative to positive charges and therefore open up an opportunity for immune T-cells, which are naturally equipped to be negatively charged, to be able to attack the malignant tumor with the body's own immune system. The problem is that the cancer's glycocalyx has a negative charge, which naturally repels the immune system's killer T-cells. A part of the solution offered via the disclosed embodiments is the ability to rearrange the negative glycocalyx to switch over to a positive charge. Hence, the killer T-cells along with other immune system features are able to attack through the glycocalyx and knock out down an important cancer cell defense.

Cancer tumors are made up of large numbers of cancer cells that reproduce or multiply at incredible speed that can span 20 minutes up to some 24 hours or longer, depending on the specific cancer species. Cancer cells continuously reproduce themselves for the life span of any given malignant tumor. A specific tumor continues to extend itself locally within the body until its blood supply and space limit its growth. Then it has to trigger a metastatic program whereby it releases outer cells of the tumor to travel to other locations where it can gather blood supply and nourishment and have enough living space to expand. All types of cells can be cancerized including neurons, bones, glandular and connective tissue, muscle, organs, and skin, nothing is exempt.

There are no prior systems that accomplish reprogramming of the intra-cellular communication system of cancer cells and specifically the nuclei of each malignant cell by means of electrically manipulating the signals and disabling them by use of confounding electrical signal shapes. The present inventor was the first to outline such a system and approach in other patent filings. The cancer treatment signal operates at the approximate voltage and amperage level of the cancer cell's nucleus. Also it is known that the cellular mechanisms and organelles operating within the cytoplasm share electrical signal encoded language of all the cells in a tumor. Encoded electrical signals participate in the life, death, growth, and reproduction activities, from the plasma membrane to the nucleus of each malignant cell living within the tumor.

The disclosed embodiments are designed to cause necrosis, apoptosis, karyolysis, pyknosis, and/or then karyorrhexis in multiple clusters of cells simultaneously by application and distributing or transporting the confounding treatment signals throughout the tumor. The communication links include the entire cellular cytoskeleton and pathways provided by desmosome, gap junction and/or tight junction linkage between the adjoining tumor cells. In that manner the signals are distributed to every element of the tumor so they supply like-kind treatment operating information throughout. However, depending on the size of the tumor at least 1 repeat application of the reprogrammed signals may be required for a complete exposure to cause programmed cell death throughout the cancer.

As part of the cancer destruction treatment is the introduction of calcium into the nucleus to assist in triggering the nuclei of the tumor to undergo and participate in the apoptosis, pyknosis, and karyorrhexis cellular events.

Understanding Cancer Cells and a New Technology to Destroy them

Electrical and Encoded Signal Aspects to Kill Cancer Tumor Cells

Figure 2:
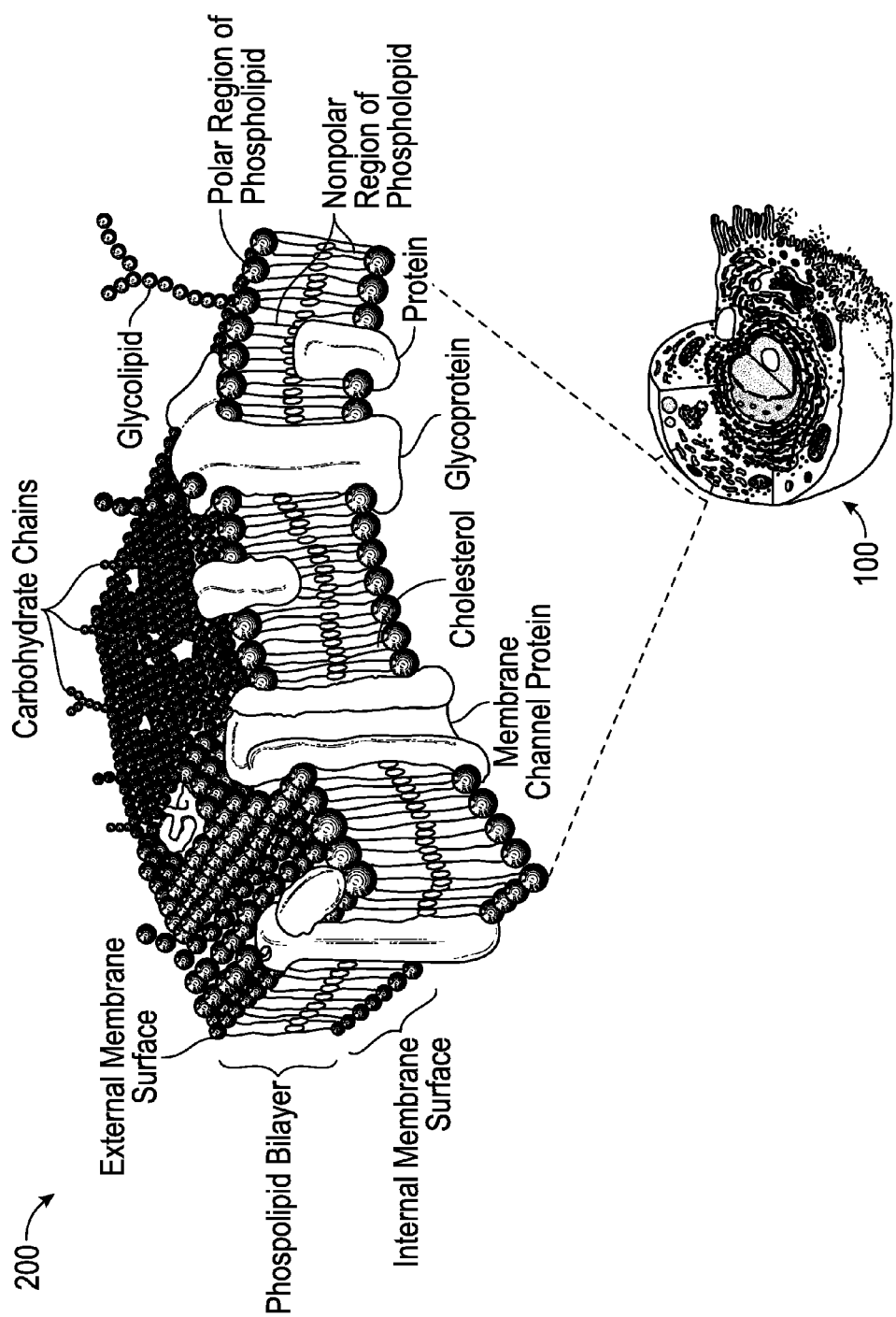
FIG. 2 illustrates a pictorial drawing of the structure of the plasma membrane.

FIG. 1 illustrates a schematic drawing of cellular components of an example cell 100. The depiction shown in FIG. 1 illustrates, for example, cellular components such as mitochondria, ribosomes, centrosome, centrioles, the nucleus and nucleolus, and so on. FIG. 2 illustrates a schematic drawing 200 of the structure of a plasma membrane 100 of the cell 100 shown in FIG. 1.

Cancer cells have a complex cellular wall called the plasma membrane, an example of which is shown in FIG. 2, and which surrounds or spreads over all sides of the cell 100. There are some 300 types of ion pores in the plasma membrane for purposes of transporting all of the raw materials used by the cell to live and compound the materials used by the cell to perform its duties.

The plasma membrane may have from a small number ion channels up to approximately 200 to 400 molecular channels or more and of different dimension though which the passage of desired nutriments and electrolytic ions can enter the cell. In addition, the selected ion channels can rid the individual cells of waste products in a process called autophagy to transport, excrete or see to the expulsion of waste products from the cellular interior into the extracellular space.

The molecular channels within the plasma membrane have molecular sized opening for the different molecules of extracellular ions and other nutriments or materials required by the cell. An example of the materials desired by the cell would be sodium, potassium, magnesium, calcium ions, and water.

The numbers of molecular channels are individually only able to admit selected sized ions and molecules and are present in the numbers that approximate the amount of ions and molecules that are required by the cell.

The passage of ions through the cellular membrane participates, generates and/or creates a flow of electric currents within the membrane and/or on the inner surface of the plasma membrane. At points where the cytoskeleton, intermediate-filaments or microfilaments is attached to the plasma membranes it allows the signals to gain entry onto the cytoskeleton so as to be able to serve as a pathway to transport the signals around the cell. The signals travel to trigger or adjust chemical reaction areas and to various organelles and the nucleus to trigger reactions and pass along cellular communication instructions, at a minimum.

The cancer cell membrane is both the site and the source of the intra-cellular electrical energy that operates the signaling processes within the cell. So it might be the that the cell wall plasma membrane anatomy is the actual generator of the electrical energy and helps form the shape of the signal(s) that operates within a particular cell. All of the malignant cells combined electrical energy that is generated in or around the plasma membrane provides for a communication system not only within a given cell but throughout the entire tumor by means of the conductivity of the cytoskeleton as it passes from one cell to another via desmosomes or other special connections established between the connected adjacent cancerous cells.

This electrical signal flow traveling throughout the many cells of the tumor allows for the generation of instructions to selected cells that are destined to metastasize to distant sites to spread colonies for the malignancy. Such cells become soft and slightly puffy as they are released into the lymph or blood circulation system to travel to distant sites to start a new metastatic colony.

Other signals are generated when a tumor gets to a certain size and is unable to receive enough blood flow to nourish the rapidly growing malignant mass so as to trigger nearby blood vessels to generate and project additional or larger arteries directly into the tumor. In response to encoded signals from the tumor smaller arterial branches will bud from larger blood vessels and extend into the tumor where it will splay into multiple arteries and enter the tumor at desired locations to deliver blood with its oxygen to the parts of the tumor cluster that are becoming hypoxic. Without the additional blood supply the tumors destiny will be impaired and many cells may eventually die. Otherwise the tumor would have to limit its cell multiplication to hold down the growth size of the malignancy to accommodate to the level of available blood supply.

This disclosed embodiments make use of a reprogramming of the above mentioned electrical signal process to be able to alter the shape and electrical properties of the cellular system and the system of signals throughout the tumor cellular cluster in a given location of a human or animal body. The most desirable signal alteration would be aimed at causing cell death by how the treatment signals are reshaped to disturb the metabolism, nucleolus communication, protein manufacturing and reproduction mechanisms simultaneously so as to prevent the cell from resuming its normal duties. First, certain cell signals are recorded and then altered by reprogramming the shape and power level of the resident cancer electrical system from the malignant cell is accomplished. Secondly, the treatment codes are transmitted into the malignant tumor along with the calcium treatment.

Calcium C++ Applied to and Inserted into the Cancer Cells

C++ calcium of the finest size particles, preferably as close to molecular size are made up into liquid slurry for painting onto the tumor or compounded in a form so that a C++ formulation can be sprayed over the tumor with a miniature spraying apparatus with adjustable or changeable nozzle to meet the location and size of the tumor(s).

Figure 5A:
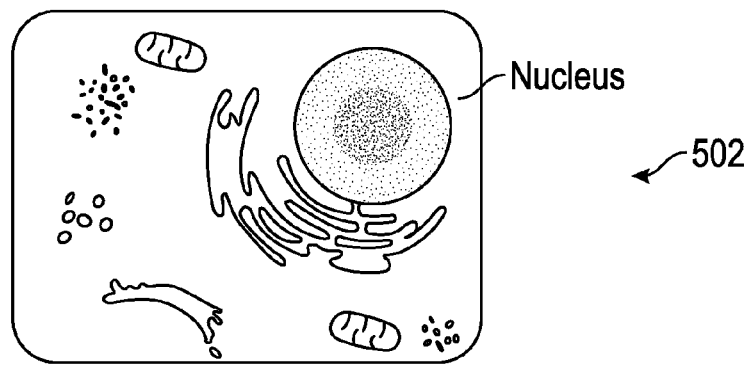
FIG. 5 illustrates a schematic diagram depicting apoptosis, pyknosis, and Karyorrhexis events.
Figure 5B:
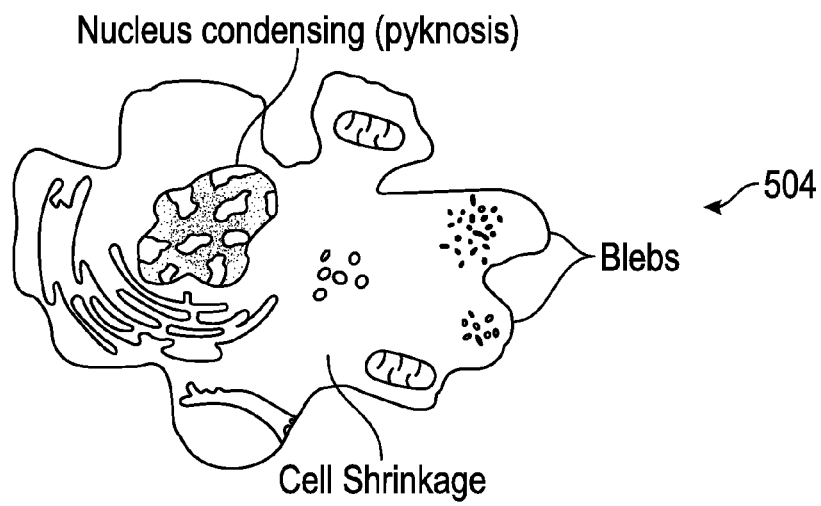
Figure 5C:
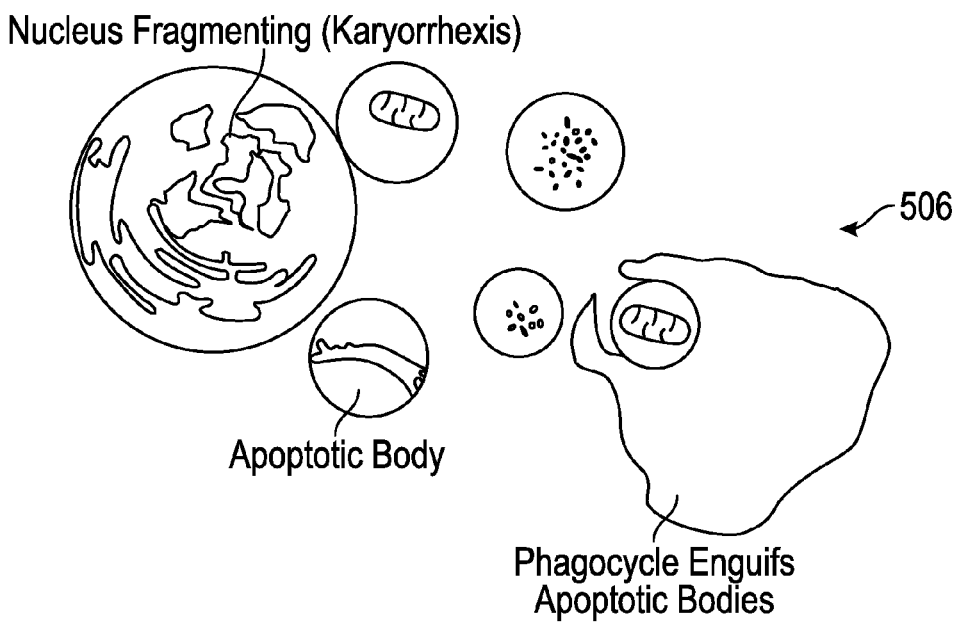
Figure 6:
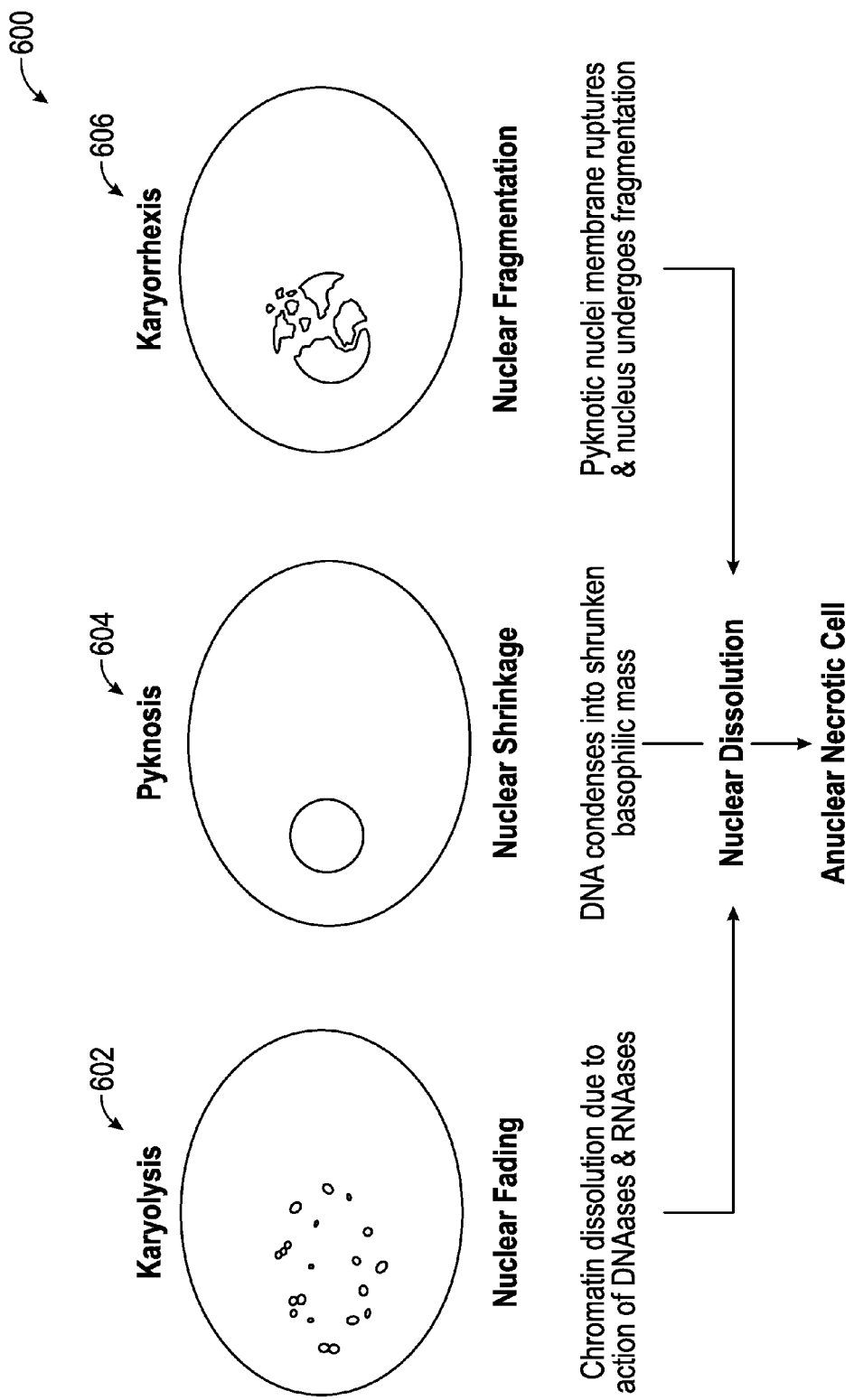
FIG. 6 also illustrates a schematic diagram depicting karyolysis, pyknosis, and Karyorrhexis leading to nuclear dissolution and an anculear nectroic cell.

The C++ calcium slurry or compound will smooth only the cancer target of the treatment. The contact of the C++ calcium that contacts the calcium ion channels will be taken into the cell while the coating over the other channels who's pore size will not accommodate the calcium particle dimension would smoother and prevent the usual other ionic particles from entering the cell(s). Such increasing of the calcium in the cells coupled with the denying of other ionic molecules to cellular duties will contribute to injuring the cell by osmotic shock and moving it to its death status by apoptosis or karyorrhexis. FIG. 5 illustrates the basic components of a cell 502 including, for example, a nucleus. Pyknosis 504 or nucleus condensing is also shown in FIG. 5. Karyorrhexis 506 or nucleus fragmenting is also shown in FIG. 5. Similarly, FIG. 6 illustrates a schematic diagram 600 depicting karyolysis 602, pyknosis 604 and karyorrhexis 606 leading to nuclear dissolution and an anculear nectroic cell.

Figure 7:
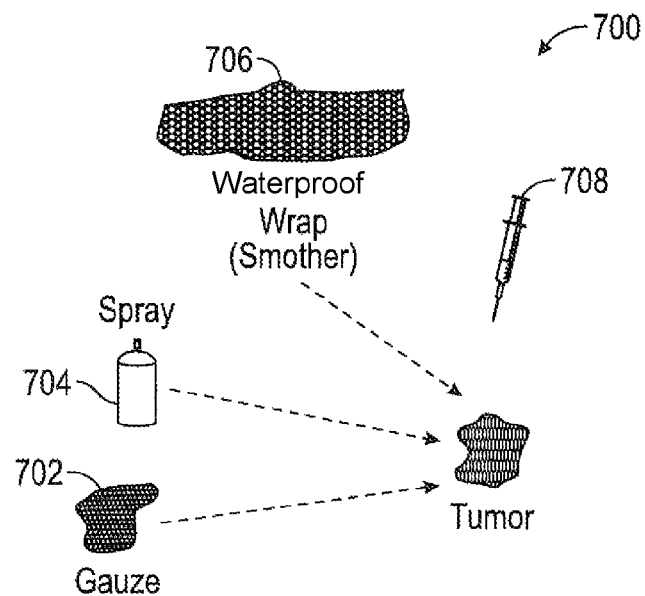
FIG. 7 illustrates example devices capable of applying C++ tumor treatment compounds, in accordance with the disclosed embodiments.

FIG. 7 illustrates example devices capable of applying C++ tumor treatment compounds, in accordance with the disclosed embodiments. For example, FIG. 7 indicates an example tumor 700, which is located within the body of a patient. Potential devices include, for example, a miniature spraying apparatus 704, such as described above. The use of C++ calcium as part of the method to cause the death of the cancer may be applied by many techniques, including injection, painting by brush or sprayer, wrapped cloth or gauze 702 impregnated with the calcium compounded formulation. Also, the C++ calcium is coated the required amount of times around the tumor and can then be sealed with an impervious or breathable material to prevent waste products from exiting the tumor. In addition, the wrapping treatment via such a waterproof wrap 706, for example, prevents any extracellular ions or water from entering the tumor 700 proper. Such a treatment smothers the malignant tumor and prevents it from receiving anything but the calcium which will have a tendency to accelerate or excite the cancer cell's internally generated operational electrical signals which will have the effect to drive the participating malignant cells toward apoptosis and karyorrhexis which will lead to fragmenting the nucleus and the death of the cancer cells in places which have been treated, as described. In other situations, the calcium may be injected via a syringe 708 directly into the tumor in association the with electrical cancer treatment described herein.

Brief Introduction to Normal Cells

All humans and animals are constructed of cells. Cells are the smallest fundamental unit of life. A cell is the smallest living structure capable of performing all of the processes that define life. All cells have an electrical and a chemical process. Most cells have an electrical communication system to operate the cell. The human body is made up of some 100 trillion cells representing perhaps some 300 cell-types. Each cell-type performs a specific function such as operating muscles, glands, and vital organs. In addition, nerves, which are made of communicating-cells called neurons, provide electrical regulating signals to operate and adjust enormous amounts of functional activities throughout the body to maintain homeostasis (life equilibrium).

Normal cells reproduce by going through a cell cycle that leads to reproduction of similar cells by a process of mitosis which is where a single cell divides and then splits into two daughter cells that are exact replications of the mother cell. Normal cells are limited as to how many times they can reproduce by mitosis, which is probably no more than 70 times.

Brief Introduction to Cancerized Cells:

Cancer occurs in normal cells which birth-defected distorted chromosomes and abnormal genes which lead to the formation of a defective cell which exhibits a severe disorder of mitosis (cell division). The thrust of a cancerized cell is to continuously reproduce by splitting into similar daughter cells uncontrollably, for its entire life. Some species of cancer cells can reproduce continuously every 30 minutes while other could take 24 hours or longer to multiply each cell that is undergoing reproductive mitosis. When a cell becomes malignant, changes are made in its electrical communication signals.

Once a normal but defective cell becomes cancerized, it has a tendency to grow a colony of similar cancer cells without regard to its former normal cell duties and destiny. Defective normal cells that have the potential to become cancerized can be potentially triggered by a number of factors such as cigarette smoke, chemicals, viruses, radiation or other influence. So we can say that a cancer cell emerges from a normal cell that has undergone a malignant change.

Cancer cells continue to reproduce by splitting (including the nucleus) into two daughter cells which themselves split and grow into adult cancer cells and then split again, on and on continually for the life of the malignancy. This process of cell splitting is called mitosis only produces daughter cells, which enlarges into a massive collection of cells, which we call a tumor. Designated cancer cells on the outer edges of the tumor can be released and travel to other distant sites by a process called metastasis. Once this metastatic process proceeds, the cancer spreads to critical body parts and usually heralds a poor overall outcome for the patient. Cancer cells are unregulated, disorganized, and engage in extremely rapid rates of mitosis. When enough cancer cells are made, they form larger tumors, which interfere with the duties and nutrition of nearby normal cells.

Cancer does it's damage in complex ways that include strangling or distorting organs, blood vessels and nerves as well as working its way into bones, brain, and muscles. Groups of cancer cells are connected together and feature an inter-connected electrical communication system internally and between each of the cells within a malignant tumor. Cancer cells perform no function that contributes to the homeostasis (life equilibrium) of the body, in any way.

Cancer cells have developed ways to repel the human body immune system by several means including erecting an electrical shield on the outer surface of the plasma membrane, which is produced by the cancer cell itself. Such thin electrical shield is called the glycocalyx and generates a negative charge to oppose the animal or human immune system, which is also negatively charged. Two negative bodies repel each other, which in the case of cancer means that the immune system cannot engage the tumor to destroy it. The body's natural immune system is not effective in attacking cancer as it does in attacking invading bacteria or viruses or even malfunctioning cells that have been injured, which are usually positively charged. Positively charged microbes or ill cells are susceptible to killer T-cell and other immune system attacks because the negatively charged immune defenses can approach its target successfully.

Anatomy and Physiology of Cell Components

The Plasma Membrane

A characteristic cell is surrounded by a thin plasma membrane, which separates the internal structures and operating organelles from the cells external environment. It houses and protects the contents of the cell. It consists of a bi-layer of phospholipids and various proteins, which are attached or embedded.

The plasma membrane is a semi permeable structure that allows passage of nutrients, ions, water and other materials into the cell. It also allows an exit pathway for waste products and for functional two-way passage of many kinds of molecules to adjust cell chemistry. The principal purpose of the cell membrane is to provide a barrier that contains all of the processes and components within the living cell and to simultaneously repel unwanted substances from invading or entering the cell.

Since cells are electrochemical in nature, the plasma membrane is the site for generating the cells electrical signals for metabolic and other operations and to serve as a means to communicate, relay and receive signals with other cells, especially those of similar type. The nucleus and plasma membrane communicate with electrical signals. The nucleus determines how the cell functions and also determines the architecture of the cell and its contents. The plasma membrane uses electrical signaling to open passageways and ion channels to allow the intake of chemicals as well as the outflow of cellular waste products.

The thickness of a typical cellular membrane is something like 7-8 nanometers. Because it is so thin it can only endure so much of an electrical field which does not exceed 100 mill volts, or 1 tenth of a volt. Almost certainly the electrical field would not exceed 150 mill volts to prevent a dielectric breakdown that is arcing across the membrane wall. Almost certainly exceeding 200 mill volts would produce destructive arcing.

The outside of the cell membrane is coated with a defensive glycocalyx, which is designed and produced by the cell to protect it and allow it to be recognized. The nucleus has input into the crafting of membrane defensive characteristics. The Glycocalyx can produce a negative electric surface charge in cancer cells so as to repel the body's immune system.

The cell membrane regulates the flow of materials into and out of the cell. Also, it can detect external signals and mediate interactions between other cells. Membrane carbohydrates installed on the outer surface function as cell markers to distinguish itself from other cells.

Figure 3:
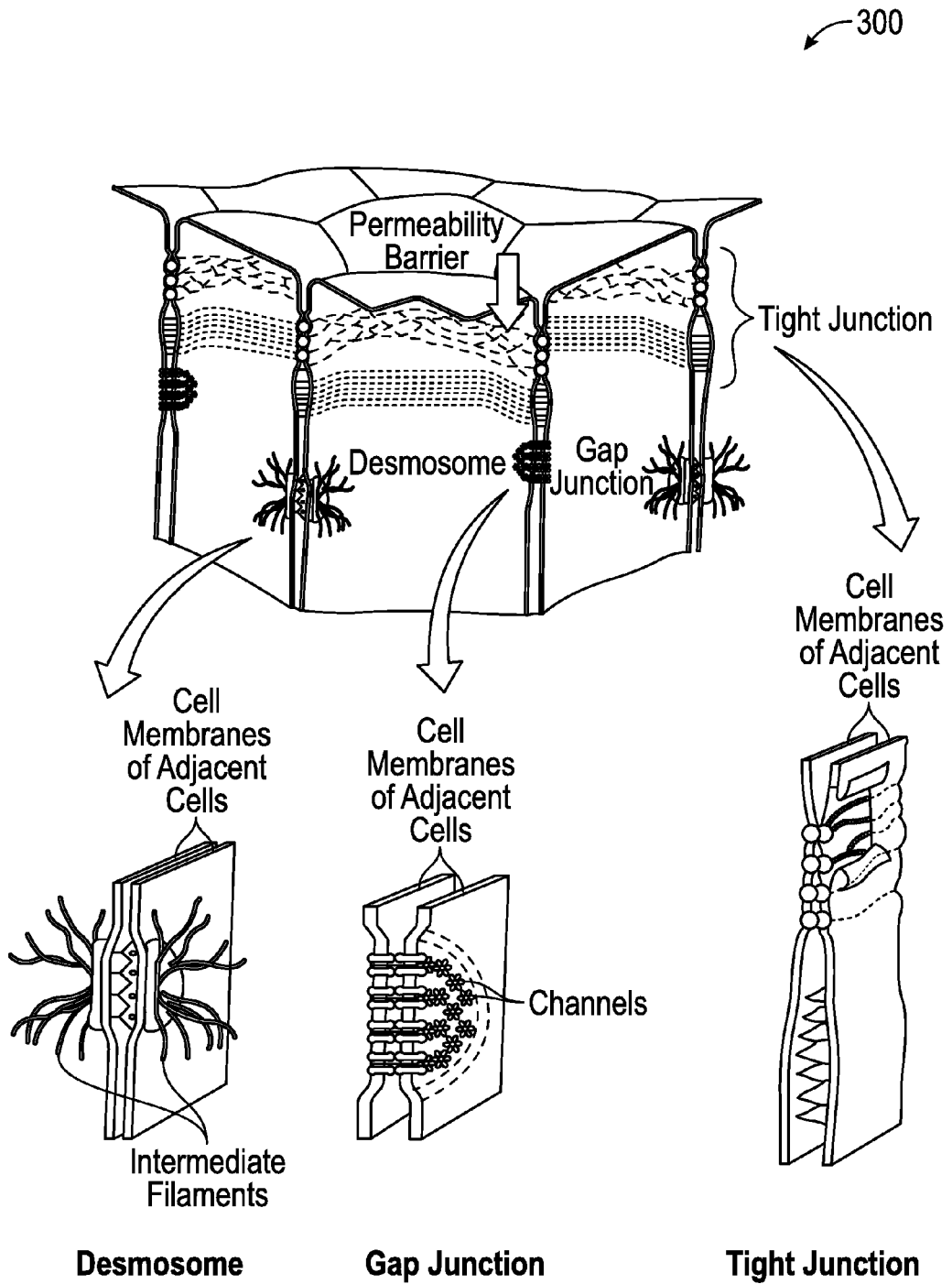
FIG. 3 illustrates a junction view of the attachments between tumor cells.
Figure 4:
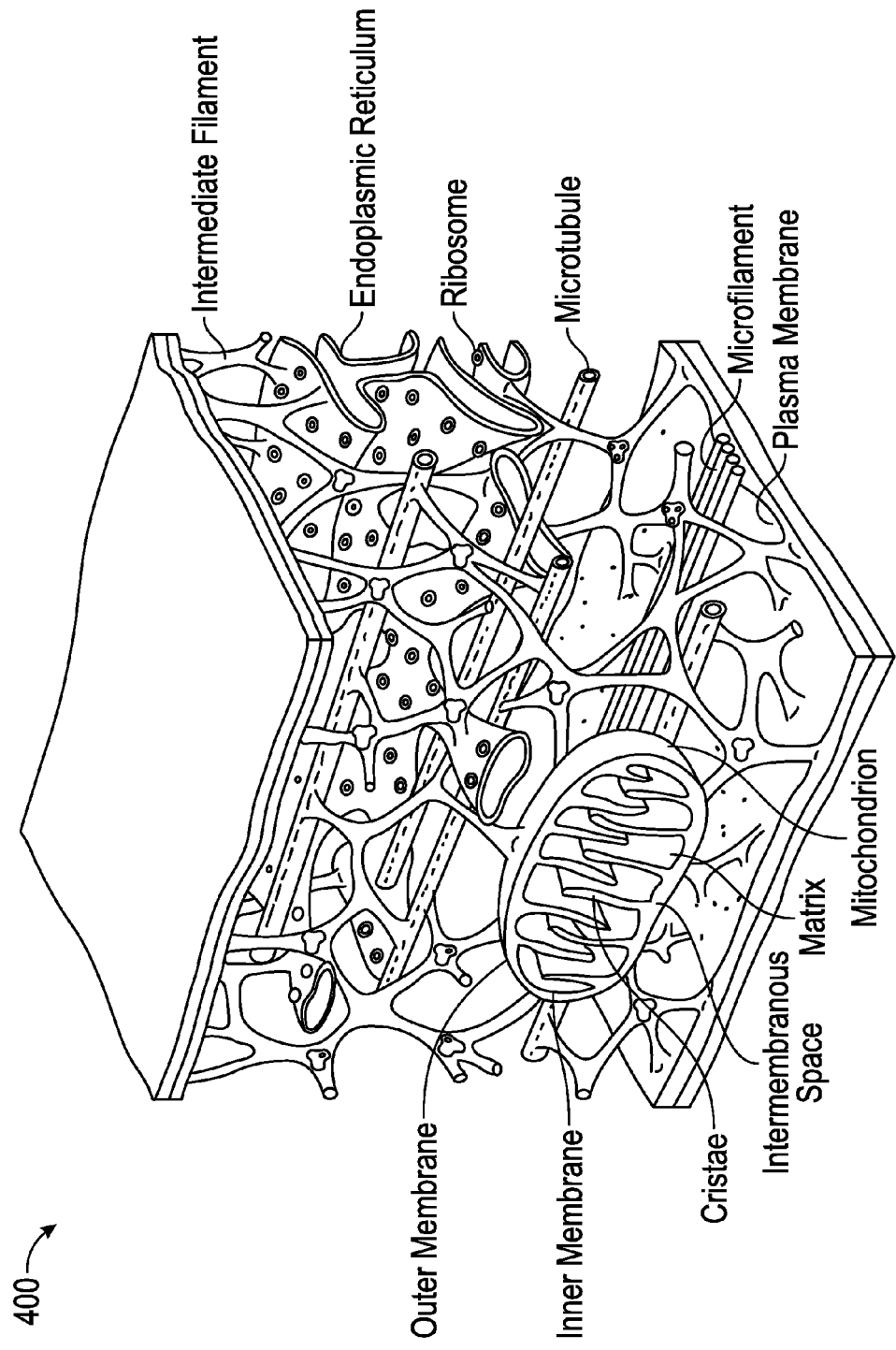
FIG. 4 illustrates a pictorial drawing of the internal framework of a cell.

This plasma membrane contains the sites where the electrical energy is created and the cellular communication signals are formed. These signals are transmitted over the cytoskeleton, which acts like wires, to regulate and trigger metabolic and functional processes within the cell. The cell nucleus communicates with all organelles and operating structures located within the cell. FIG. 3, for example, illustrates a junction view 100 of the attachments between tumor cells. FIG. 4 illustrates a pictorial drawing of the internal framework 400 of a cell, such as the cell 100 shown in FIG. 1.

Cytoskeleton

The cytoskeleton maintains the shape of all cells from the inside. It is like a geodesic structure that provides strength and internal areas for electro-chemical timed reactions. Noteworthy is that the cytoskeleton extends into other cells and links up with their cytoskeleton to maintain and form communication links into adjacent cells. This structure is made up of a network of hollow-microtubules, solid-microfilaments, and solid-intermediate filaments. The cytoskeleton is anchored to the plasma membrane and serves as the "wiring" to transmit the cellular communication signals.

The cytoskeleton is made up of actin and myosin, which are also found in muscle structures. The cytoskeleton also controls the circulation of the cytosol, which is the fluid and semi-fluid that suspends the organelles. Organelles are the functioning entities of the cell that manufacture and distribute cellular products and processes necessary for the cell to live.

Cell Communication Connections

Individual cells operate themselves by electrical and chemical processes to maintain life and to perform the function for which a given cell has been constructed. Cancer cells have different electrical signals than normal cells.

Cells generate their electrical energy and communication signals within the plasma membrane. Such membrane also has electrical connections to adjacent cells of the same type to allow uniform information transfer. The nucleus is in communication with activities occurring in the plasma membrane, for that matter all other activities of the cell. Electrical signaling functions control and regulate chemical activities, autophagy, regulates the mitochondrial production of ATP which serve as an energy source for the cell and controls the ribosome's protein manufacturing operations. In additions the electrical codes serve as communication means with the adjoining cells including when to release cells for metastasis operations among other duties.

Cell communication is both electrical and chemical. Little scientific work has been done to understand electrical cell signals, due largely to the lack of electronic equipment to detect, record, and retransmit the tiny cellular waveforms operating within the cells. Over the last century studies of cell activity was confined to figuring out how the chemical activity operates because of lack of recording and sensing techniques as well microscopic capability to study the details of what was going on.

Cytoplasm and Key Cellular Organelles

Cytoplasm and Nucleus:

The cytoplasm, a fluid that can be rather gel-like, surrounds the nucleus, which is considered an organelle. The nucleus contains the DNA genetic information and hence, controls both the activity of the cell and its structural nature. The nucleus is spherical and is surrounded by a double membrane, the nuclear membrane and envelope, which is perforated by a significant number of pores that allow the exchange of materials and substances with the cell's cytoplasm and the extra moist environment outside which contains the ionic minerals and chemicals that feed the cells and provides the necessary water.

The nucleus is an electrical body which contains the cell's DNA and carries programs to operate its electrical signals and the opening and closing of channels in the wall of the cell's plasma membrane. The nucleus also contains the apoptosis program for cell suicide. Depending on the duties of the cell, some use ion channels that function electrically and others are influenced by chemicals that it obtains from the extra cellular media. Ion pumps and ion channels are electrically equivalent to a set of batteries and resistors inserted in the membrane wall, and thusly creating voltage differences between the inner and outer sides of the membrane. Such difference in the electrical values range from −40 mV to −80 mV. Because the cell acts as a battery it provides the power to operate molecular devices that are embedded in the plasma membrane. The electrical activity sends signals that communicate with adjoining cells of the tumor to regulate the cancer as an intra grail living body.

Mitochondria:

An important organelle is the mitochondria, which serves as the power station for the cell. They are rod or oval shaped structures functioning as respiration for the cell. A number of mitochondria are scattered within the cytoplasm and move in accordance with its flow. The product produced as a biological fuel is called adenosine tri-phosphate (ATP). The manufacture of ATP results from the processing of proteins, fats, and carbohydrates. The cell communication system supplies the ATP to other organelles that require this bio-fuel to provide processing energy as needed.

Endoplasmic Reticulum (ER):

Is a network of membranes that form channels that crisscross the cytoplasm utilizing its tubular and vesicular structures to manufacture various molecules. The system is dotted with small granular structures called ribosomes for the synthesis of proteins. Smooth ER makes fat compounds and deactivates certain chemicals like alcohol or detected undesirable chemicals such as pesticides. Rough ER makes and modifies proteins and stores them until notified by the cell communication system to send them to organelles that require the substances. All cells in humans, except erythrocytes (red blood cells), are equipped with endoplasmic reticulum.

Golgi Apparatus:

Consist of Golgi bodies, which are located close to the nucleus and consist of flattened membranes stacked atop one another like a stack of plates. The Golgi apparatus sorts and modifies proteins and fats made by the ER, after which it surrounds and packs them in a membranous vesicle so they can be moved around the cell as needed. Similarly, there is a process to pack up cell waste products for expulsion from the cell via ports in the plasma membrane into the extra cellular spaces.

Lysosomes:

Are the digestive system for the cell. They contain copious quantities of acids, enzymes, and phosphates to break down microbes and other undesirable substances that have entered the cell. They also digest and recycle worn-out organelles to make new cellular structures or parts.

Ribosomes:

Are tiny spherical organelles distributed around the cell in large numbers to synthesize cell proteins. They also create amino acid chains for protein manufacture. Ribosomes are created within the nucleoli at the level of the nucleolus and then released into the cytoplasm.

Programmed Cell Death

Programmed cell death is called apoptosis. Apoptosis as a bio-medical term indicating that there is a state of natural or induced reprogramming of a cell to enter a suicide mode whereby the cell dies without any inflammatory process. Thereafter, the lifeless cell is phagocytized and removed by macrophages of the immune system. Apoptosis can occur in many kinds of cells such as erythrocytes as a method to rid the body of non-performing or defective cells. Cancer cells are thought to not have much opportunity to have preprogrammed cell death because those cells have an immortal ability to continue to reproduce and reorganize the cellular electrochemical system in a way that suits the purpose of the cancerized cell. However, the inventor is aware that cancer cells do get diverted to activate programmed cell death and destroy themselves in response to an abnormal birth. It does this to commit suicide so as not to burden the well-formed cancer cells, which are capable of participating in the life process of a growing tumor cluster.

Cancer Cell Activity

Although some 200 ion channels or more that populate all sides of the cell plasma membrane which encompasses and shelters the interior operations of the cancer cell. All cells, including malignant ones, must have an internal signaling mechanism in order for them to operate the cell and remain alive as well as participating in tumor life processes of continuous reproduction of more cancer cells. Any individual cell is among the smallest units of life. Cancer cells generally have signaling ability to adjacent similar cells so they can be coordinated to work together. Their principal duties are the bringing into the tumor sufficient oxygen and nutriments to support its principal goal of unending reproduction by mitosis (Karyokinesis). This is a method of nuclear division, which produces two daughter cells by a process of cell division. This is the usual process by which nuclei are replicated in the orderly process of mitosis as one cell becomes two. This is accomplished by splitting the plasma membrane, cytoplasm and organelles of the parent cell into two distinct daughter cells.

Signaling between cells of a tumor makes it possible to know when to release adult cells so that they can metastasize to other areas and begin a new tumor colony. The metastatic cancer cells travel within the blood vessels or the lymphatic system or propel themselves across an organ, nerve, gland, or muscle to seed a new tumor site. For the individual cancer cells to communicate among themselves they have to establish links to neighboring cells. These connections between the individual adjacent cancer cells are specifically tied to one another to allow for the sharing of signals. Ordinarily, cancer cells do not communicate with normal cells and are unable to operate the healthy normal cell in any way, therefore sparing the unaffected normal cell from any direct operational assault.

An initiating cancer cell starts out as a normal cell but develops a chromosomal and/or a genetic chaos that drives a transformation to malignancy. Prevailing cancer theory blames mutations in important regulatory genes for disturbing the normal controls on cells that are destined to become malignant. Such theory does not give credit to the damaging changes to actual chromosomes that are seen in all cancer cells. The distorted, broken or bent chromosomes unbalance thousands of genes en masse and are sufficient to trigger cellular instability that leads to serious genetic disruption and to account for the transformation of so-called normal cells into malignant ones. The cancer cells retain their electrochemical signaling and operating systems which existed when it was a normal cell, but now changes are ordered up for it to rearrange its cellular mechanisms in new ways to disconnect its communication ability from adjacent normal cells and to start rapid reproduction of more cancerous cells which are then connected to communicate only with in its own transformed malignant species.

Interestingly the first cancer cells that are adjacent to normal unaffected cells are sometimes not wired into the rest of the tumor. Perhaps these first cells are only a demarcation line from malignant to normal and do not have to participate in the cellular communication system. Later cells do develop the desmosome interconnection communication system that allows a way for each cell to speak to its adjacent neighbor cells. Other means of communicating between cancer cells beside desmosomes are gap junctions, direct cell connections and tight junctions. The various junctions are connected with the intermediate filaments so as to provide the pathway to transmit messages between the various cancer cells.

Neither the normal cell nor the malignant cell can live without a functioning electrical signaling mechanism to operate the electro-chemical processes that are shelved on the cytoskeleton shelving. The cytoskeleton is the framework within the cell that provides a somewhat flexible geodesic-like framework to maintain cell shape, provide shelves for chemical or electrochemical process and allow space for the organelles, nucleus and protein manufacturing elements within the cell. The liquid within the cell is called cytoplasm. There is a cytoplasmic streaming process that causes directional movement of the liquid cytoplasm as a means of local transport for the semi-floating organelles (functional cell components). Likely this allows these floating structures some sort of communication between the cellular membrane and the nucleus as they come into close proximity.

The cytoskeleton is composed and constructed of intermediate sized filaments, which actually serve as the internal structure to maintain cellular shape. But for our purposes, we know that the filamentous structure serves to provide a highway for electrical signals to travel to sites of chemical process that reside on shelves constructed by the cytoskeleton assembly within the cell. The intermediate filaments are composed of compounds that are similar to the structures of muscles, which have their own electrical properties. The signals traveling through or on the cytoskeleton most likely initiates and stops the chemical reactions, as required. The electrical signals likely skip and travel along the surface of the filamentous network rather than within the central framework, again on some sort of scheduled or timed basis or in response to some event or instruction. Access to all systems within the cell by nucleus operations is made possible by electrical signals residing within the individual cells. The cells communicate with all the adjoining living cancer cells.

Cells become more electro-negative in the course of cancerization, which no doubt is genetically mediated. Cancer cells seem to reconstruct the cellular membrane access ports to allow the importation of more sodium and sugars than non-cancerous cells of the same size. The electrical potential between the inner and exterior layers of the plasma membrane serve as a sort of electrical generator to supply the power to operate the individual cancer cell The cytoskeleton intermediate filaments are hooked together with a sort of "Velcro" at its connection points throughout the cells interior to allow some flexing of the overall cellular structure. Importantly, the intermediate filaments continue protruding through the desmosome which allows a connection to an adjoining cancer cell. This piercing of the cell wall within the desmosome is how signals are sent and received from adjoining cells. There can be several desmosome connections on different aspects of the cell wall (plasma membrane) so as to connect to cells over, under and beside a given cancerous cell, so as to communicate with everybody. In the alternative, other types of cellular attachment for signal transduction or transmission is likely. We can never forget that every cell is a unit of life unto itself and has the ability to accomplish some sort of simple primitive reasoning or organized processing that is not understood at this time.

Japanese scientists have performed a great deal of work by microscope that dates back into the 1980s on various cellular attachment schemes. Ishimaru, Kurano and Hayashi, for example, noted that some cells in a haematoma/sarcoma tumor island had no desmosome connection while they found that a great many cancer cells do utilize desmosome connections. The Japanese scientist also reported that some of the cells formed island-like structures, the cell contact to normal cells in the structure consisted of only simple apposition with no intermediate junctions, desmosomes or tight junctions. Which means there is only minimal interrelationships. They in a sense became mere barriers between normal and cancerous cells. (Reference—Cancer Cell Biology, edited by Takeo Nagyo and Wataru Mori, published by Japan Scientific Societies Press, Tokyo. ISBN 4-7622-0250-2 Published December 1980).

Besides being a barrier, cells that are attached on the outer edges of the tumor are the non-desmosome-connected type and may become the cells that would be released to metastasize, although no one has suggested that. The Japanese did note that cells on the peripheral of an aggressively growing cancer did not have desmosomes inter-cellular connections but were assembled by tight junctions or intermediate junctions mechanisms. It is not known as yet, if cytoskeleton connections touch the point of other types of cellular adhesion as a communication link to adjacent cells or make the transition connecting in mid-desmosome. There is suspicion that all the abutting cancer cells are able to communicate with one another. It is suspected that cancer cells that are going to metastasize do prepare themselves to split-away from the tumor duster. Especially when the cells are beginning to starve for blood flow and oxygen. We have a report that as the cell gets ready to metastasize, it becomes more compressible and "squishier" according to James Gimzewski of UCLA in a report released in December 2007. Presumably this is a part of the metastatic process of breaking away from the mother tumor to travel elsewhere via the lymphatic, vascular system or by direct extension from the primary tumor site to a nearby region that the cancer deems a suitably fertile area to colonize and develop a plot for a brand new tumor. It seems that there are preferred areas that specific kinds of cancer select to establish their various metastatic colony.

It is not known how signals went through to other cells when desmosomes connections were not in attendance. Potentially some other types of cell wall connections allow for the transfer of electrical instructions such as releasing to go and metastasize or to take on reproduction duties. Electrical signals from the plasma membrane travel on the surface of the intermediate filaments and reach chemical processes and likely ignite or stimulate a reaction that contributes to reproduction, protein manufacture or metabolic operations. Without electrical activity and the molecular devices that operate the cell plasma membrane, the cell could not function properly. We always have to remember that all cellular biological processes include electricity and chemical processes. There are no living cells that do not comprise both a chemical and an electrically based methodology to maintain functional operations as their purpose in life. The cell biologists are aware of this but have never launched an effort to figure out how the electrical component works. They are too invested in chemical actions and reactions as that is how they began before the age of electronics made it possible to actually trace electrical phenomenon in cells.

Cells have an electrical zone, parts of which concern the plasma membrane, which is sometimes also referred to as the cell wall. The cytoskeleton is anchored to the inside of the plasma membrane wall and serves as a method to generate or produce electrical instructions and well as seeing to distribution of the actual electrical communications.

Between the inner and outer cell plasma membrane there is an electrical potential. The cell wall seemingly can be considered a sort of battery. In fact the plasma membrane outer and inner surfaces seem to be involved with the ion ports in generating electrical signals that are involved in operation of the cell itself. Intermediate filaments and microfilaments are likely carrying the signals generated within the outer and inner plasma membrane walls and the circular ion port walls.

In cancers the charge of the outer wall takes on a protective negative charge, especially on the very thin outermost cell coating which is called the glycocalyx. This glycocalyx in cancers have a continuous negative charge protecting the malignant structure from the immune system which is also electrically charged in a negative format to repel the immune system from attacking the cancer. While non-cancerous glycocalyx coatings are positive in their protective electrical charge. All of this allows the positive protective charge to permit the negative charged immune system to embrace magnetically the positive cell protective elements and engage undesirable invaders like viruses or bacteria. Not so for the cancer glycocalyx with its negative shield which will automatically repel the immune killer T-cells as they approach.

Thusly in the laws of magnetic forces, positive and negative will join together. While negative against negative will not make a connection but would repel one another. This allows the cancer protective glycocalyx to keep the immune system forces from interfering with the malignant activity of the cancer cells.

The question comes to mind as to why have cell biologists concentrated on chemical signaling for the past 100 years?Only mentioning the likely existence of some sort of electrical process. With microscopes the scientists pursued every corner of the cell, including cancer cells to learn what was going on. They also were able to name the anatomical parts of the cell and study at least some of the chemical reactions that occurred on some of the cytoskeleton shelves. But what they could not do is determine anything about the electrical component or the contribution of an electrical signal at a given place within the cell. When they did not have full answers they just slid over to the next reaction and did not answer how the complete communicational process operates. It was easy then in those historical times to merely say, it was communicating only via chemical signals.

Gradually university cell researchers and teaching teams continued with the chemical reaction theory, but were usually unable to actually initiate or cause any individual cellular communication reaction to occur in a laboratory setting. Cellular biologists were able to analyses and identify the presence of many cytokine, ions of sodium, potassium, and calcium among others. Anytime sodium and potassium are present, one can rest assured that an electrical process is taking place. Sodium, for example, is always involved in sparking signals, as it has no other real purpose in cells, to the present inventors knowledge, except to make things move or to serve as a signal to make something happen. Always recall and remember that the cell is a little tiny unit of life which requires a great deal of preparation and the use of various types of microscopes to properly peer into and study. Think of 60 to 400 cells occupying the space taken up by a ballpoint pen dot and you can imagine how difficult it is to study a single cell. The light microscope was used by Robert Hooke during the 17$^{th}$ century to study cells. The electron microscope first introduced by Ernst Ruska in 1933 enabled cells to be explored at up to 50,000 times magnification.

The Invention of the Electron Microscope

The tunneling microscope invented in 1981 by Binnig and Rohrer in IBM's Zurich laboratory has taken the idea of studying a single atom or subatomic particle into the realm of possibility.

But even though one can see the anatomy and components of a single cell today it is still impossible to "see" the electrical process going on without a method to record and manipulate its neuro signal patterns for study. For the technical approach to be able to send a signal to trigger a cancer cell to cause apoptosis (programmable cellular death) also requires specialized electronic equipment as is described here in as the method for recording, storing, reprogramming and re-transmitting the treatment signals including versions of the imulus contact/treatment device. Because of their high conductivity and strength, carbon nanotubes, for example, can serve as a suitable contact electrode of the imulus so as to pierce a cancer cell so as to communicate with the cell nucleus. The small diameter of the imulus carbon nanotube contact electrodes provide the delicate structure to deal with the exceedingly small individual cancer cells. It can be appreciated, however, that other types of devices may be used in place of carbon nanotubes.

These contact points have made all the difference in the ability for spearing and piercing the membrane and to get inside the cell for both collecting communication signals and to transmit re-programmed signals. The carbon nanotubes may also act as antennas in the extremely wet environment of the cell. The signals are extremely fast and ultra-low voltage at micro amps. The signal will be so small that a human would not be able to detect it from a single nanotube electrode which was in close contact with a sensitive fingertip. It is not the power of the signal that is important but rather the shape and configuration of the transmitted treatment signal that is important. There is little doubt that we can gain control of a cancer cell electrical process, at least to the point of wrecking cell mechanisms with what we know now.

Since the cells are interconnected with each other it is believed that we will affect many cancerous cells simultaneously by insertion of carbon nanotubes into at least some of the cancer cells. 10,000 carbon nanotubes laying side by side would equal the diameter of a human head hair. They are sharp, as strong as steel and have the conductivity of copper—the perfect electrode. The imulus receives the reprogrammed cellular communication signals and utilizes its pattern of carbon nanotubes as the entry vehicle into the cancer cell cluster or island. It is not known how many treatment applications will be needed to destroy all the cancer cells at a given site. The treatment application will be brief, allowing for re-application and treatment of adjacent cells.

The certain reason for why scientists have not studied cellular electricity is that there was no proper electronic equipment in existence until the 1990s that could possibly detect, record and allow transmission of these ultra-low power very fast signals to properly study electrical aspects and their contribution to cellular processes. Since the cellular and biochemists were so invested in the concept of chemical reactions being the communication methodology for cells that they never approached electrical activity as a partner with chemistry to operate cell life. Electrochemical process abound within operating and fast reproducing cells.

Likely even the simplest cell that take up space or are part of the connective tissue there has to be some sort of electrical process to maintain its metabolism and plasma membrane operations. We doubt there is any cell that does not have an electrical process working away, continuously.

Neurons have an electrical signaling process and a cellular electrical process. Most other cells, such as cancer cells would only have an internal electrical operating process. It is possible that cancer cells are able to communicate to blood vessels to encourage them to extend and direct a new vascular connection to grow into a cluster of cancer cells to supply more oxygen and nutrition needed to match the pace of reproduction and need for nourishment.

Cellular systems are completely controlled and regulated with strict electrical signals that duplicated, or are similar to the natural electrical messages that have been in existent from the earliest beings of multi-cellular organisms. There are signals that require organs do their job and also signals that report to the nucleus of the involved cancer cells acting as a brain of sorts to provide status report as to how well functionality was happening. In fact the cells that coordinate all of the organs simultaneously and confirm that body homeostasis (life equilibrium) was in good order.

The cell or cancer cell also has some sort of feed-back mechanism to insure that metabolism, cell transport of food through the plasma membrane, as well as the out-casting (excretion) of cellular waste along with reproduction, metastatic cell release and propulsion of organelles within the cytoplasm could also be ordered up in accord with a sort of grand operational plan. The tumor thusly duplicates the mechanism of the relationship of all the structures and parts that make up a living human. The cell is the smallest example of life and co-ordinate many aspects of its tiny self just as a human functions by directing the symphonies of human life.

Cell Signaling and Cancer Cell Life Operations

A cell is the smallest unit of life. Groups of cells make up multi-cellular organisms. The human body is made up of some 100 trillion cells. Cells utilize electrical and chemical signaling in operating interior and exterior mechanisms depending on the composition of the cell. Some cells are operational and signal to the brain and receive signals from the brain to regulate muscles, gland, and vital organs. Other cells only take instructions from the brain while organs and glands confine their cells to dedicated processes concerning the maintenance of life. Certain nerves and their cells are dedicated to sensing internal body status or seek information from outside the body, all with electrically encoded signals. The electrical cellular signal pattern of a malignant as well as a non-malignant cell must be able to be detected, recorded and it must be reprogrammable to access operational control of critical nucleus activity.

Cancer cells, operating as an organized tumor structure do not conduct or exchange signaling processes with normal cells. They do, however, communicate with other cells within a given tumor. They focus on their own interior signaling and metabolism while communicating with adjacent cancer cells. Cancer cells do not participate in any operational functions within a human or animal body except among themselves. Cancer cells do not aid or do anything beneficial for a human body. They are selfish and only live to reproduce and steal nutriment and oxygen from the body in which they reside.

Cancer cells, as they form a malignant tumor, require more blood flow. To accomplish this, they have evolved a way to signal to nearby arterial blood supplies so as to order-up the formation of buds on the artery that ultimately extend into blood vessels that travel over to and pipeline into the tumor. With additional blood flow, the tumor continues to reproduce and extend its dominance over its primary site.

Examples of some processes that cells naturally perform via signals:
 a. Cell reproduction
 b. Encoding of proteins
 c. Regulation of growth
 d. Differentiation of the cell
 e. Internal cell communication
 f. External signaling to other cells
 g. Excretion of chemicals
 h. On or off control of secretions or excretions
 l. Timing of operations for cellular organelles
 j. Various levels of signaling within the nucleus
 k. Signals between plasma membrane and nucleus
 l. Operation of transport mechanisms in cell wall Cell signaling is accomplished by a combination of electrical and chemical interactions. Different types of cells require a varied level of signaling qualities. The creation or generation of a given cells signals begins in the plasma membrane where raw material and chemical ions are taken in from the extracellular matrix to both generate electricity and establish the signal format. The plasma membrane is a sort-of cell wall and the area that takes in the required raw material via its ion channels. Ion channels open and close to allow passage into and from the cell interior. Electrical signals are likely generated in the plasma membrane before they are sent via the cytoskeleton, all about the cell to go and participate and contribute to cell operations.

The cytoskeleton also serves as a geodesic-style dome providing a framework to shape and support the cell. In addition, the cytoskeleton serves as the pathway by which cell signals generated in their plasma membrane travel within and around the cell to do its work. In addition, communication to adjacent cancer cells could happen through connections such as desmosomes, which are extensions that bridge and allow communication between adjacent cells of a tumor. These connections act also as a pathway for the neuro-signaling cancer treatment technology to destroy the tumor.

The small size of individual cancer cells requires a variety of microscopic electrodes to record the basic communication signals which are initially generated in the plasma membrane and within each individual cellular nucleus electrical system. Transmitted treatment signals are spread throughout many cancer cells simultaneously. This represents the dawn of an entirely new treatment approach using only tiny encoded signals to destroy cancer quickly.

Normal and Cancerized Cells Operate Via Encoded Electrical Systems

The human body is made up of some 100 trillion cells. Cell theory simply states the cell is the fundamental organizational unit of life. Indeed the cells of the human or animal body represents the smallest example of actual life. All cells have electrical & chemical capability. Cells take in raw material and create energy, make protein and expel waste as well as perform some function for the body in which it lives. A rich neuro-electric encoded communication system abounds in the cells of all living bodies as a means of controlling and regulating all of the life processes and for maintaining homeostasis (life equilibrium).

Cancer cells for the most part begin life as normal cells. Although cancerized cells can begin life already in the malignant state. However, in the process of cancerization remarkable alterations in the characteristics occur, including changes in the cell electrical communication signals. In a certain way we can say that a cancer cell starts life as an ordinary cell within which resides the mysterious seeds of defective genetics which can be tricked into malignancy. This change causes the cell to turn into a malignant cell which includes alterations to its operational destiny.

During this metaplasia into cancer the cells modify their internal signaling process to meet their new destiny to rapidly reproduce more malignant cells. Whatever duty the cells had prior to their turning malignant is no longer of importance. Cancerized cells can reproduce themselves at speeds from 20 minutes to 20 hours, depending on the species.

Tumors can consist of millions, or even billions of cells. So if a million cells reproduces in 5 hours that would result in some 2 million cells, and so on as time passes. Cancers drain the oxygen and nutrients from nearby blood vessels with which to grow ever-larger tumors in the body as they go metastatic to various predictable places within the body. While cancerized cells can reproduce forever, normal healthy cells can seldom reproduce more than a total of 70 replications in their life span.

The only stimulus for tumor growth is the available blood and nutrition supply that they take in locally and those very tiny encoded signals that organize and control the operation of the tumor and its cellular members. Schuler and her team of scientists also established that there was only analog signals operating within animal and human bodies. There simply was no cells, cancer or healthy, operating in a digital mode within any living mammalian being.

Man-made electronics generally function in a digital mode. Special analog computers and medical treatment devices can be expected to appear in the marketplace.

Injury of Cells, Neurons and their Axons

Injuring nerves and their cells as a result of stopping blood flow and/or the generation of neuro-electric signals will cause loss of function. Morphological evidence of cell death usually is not apparent for about 6 hours. Operationally a neuron including its axon responds the loss of flow of their neuro-electric signals for 8 to 15 minutes before further decay depending on how serious the injury is.

All living cells depend on their blood supply and their electrical process to maintain their life activity. With any extended switch-off time of the encoded signals involved with internal life processes of a cancer cell and its nucleus can play an important part in destroying or injuring an entire active malignant tumor.

Application of Neuro-Electric Signals to Destroy Cancer Cells

With the design and construction of a special hybrid scientific computer system, including the custom software, cancer cells are ready to be accessed and reprogrammed to destroy themselves. The cancer cells will be first recorded as to their internal communication signals and then such codes shall be modified to confound the cancer's cells metabolic and signaling processes. The anticipated results are that the nucleus shall detect the treatment signals and trigger apoptosis (programmed cell death). It is expected that a cascade of Igniculus or Interclusio signals will be conducted via the cytoskeleton and desmosomes or other interconnections within a tumor to transmit the "death codes" throughout adjacent cancer cells, all of this designated to destroy the entire tumor.

It may be necessary that tumors can be killed in sections as it is not known yet how far the interclusio signals will penetrate during a single treatment. Depending on the mass of a living tumor the extent and duration of application of the treatment signals will be estimated and planned. Effective treatments are expected to take about 10 minutes and will utilize only reprogrammed cancer death-codes to cause apoptosis (programmed cell death). No conventional radiation or chemotherapy is expected to be necessary. The treatment process is accomplished by transmitting the formatted electrical signal pattern through the plasma membrane wall into the cell interior. Ultimately the electrical signal is directed into the nucleus interior itself to accomplish certain cancer cell death by karyorrhexis.

No medical scientist & inventor has as much practical knowledge and experience or creative intellectual property regarding cellular and nerve encoded systems, as Eleanor Schuler. Schuler estimates that reprogramming & alteration of the internal electrical encoded cell signals will rapidly alarm the nucleus and release or trigger it's suicide apoptosis commands in a matter of minutes, once the reprogrammed cancer cell signals and calcium applications have been placed in the correct locations. Such signals are anticipated to travel into the tumor and transmit signals that collapse its cellular communication system with death-codes.

This technology is expected to become the definitive treatment for solid cancerous tumors in mammals.

The pending patents stand alone as the pioneering intellectual property in this very special field of neuro-signal encoded medicine. It is expected that the destruction of cancer by apoptosis will spawn a very large global neuro-electric medical industry. Such technology for causing cancer cells to commit suicide is expected to largely displace the chemotherapy industry that dominates present day cancer disease treatment.

Cancer Diseases are Found Across the World and Resist Standard Treatments

Of the maladies and ailments of mankind nothing is more disappointing and terrifying than cancer. Treating malignant tumors has reached the proportions of a major $ Trillion world industry. Despite many levels of research and testing efforts using chemotherapy, ionizing radiation and surgical approaches against active cancer diseases continue to be disappointing as to any reliable, effective or rapid cures.

Some Avenues for Destruction of Cancer Cells

Necrosis, apoptosis, autophagy, stasis, macroautophagy, cell starvation, tumor reduction, shut-down of mitochondria production of ATP, consuming contents of cytoplasm, incipient starvation, blebbing, cell shrinkage, nuclear fragmentation, chromatin condensation, chromosomal DNA fragmentation, pyknosis, karyolysis, karyorrhexis. Human bodies have complex daily cellular maintenance duties to dispose of some 50 million worn out cells every day. Average adult humans operate an ever-busy apoptosis and repair system. Key elements are briefed below.

Necrosis

Necrosis is a form of traumatic cell death that results from acute cellular injury. Necrosis death of cells can happen because of infection or fever that results in the premature death of cells in living tissue. Untreated necrosis results in a buildup of dead and decomposing cell debris in the region of actual cell death. A classic example would be gangrene. Cells dying from necrosis don't follow the usual apoptosis transduction pathways.

Apoptosis

Apoptosis is the original programmed cell death technology that helps repair and model the body beginning with birth and continuing on throughout life. Some 50 billion cells die every day due to apoptosis. For example the lining of the digestive tract from the stomach lining on to the colon undergoes apoptosis every 3 to 5 days to replace the entire inner lining of the digestive tubular structures. Red blood cells are programmed to replace themselves every 90 days by undergoing killing by the spleen and the bone marrow manufacturing new blood cells and releasing them back into the blood vessels to do their work of carrying oxygen and carbon dioxide.

There are interesting and important methods to destroy cancer cells that produce one or more apoptosis events or tactics to gain control of the cellular electrical system. Regarding the key target of a living malignant cell is the nucleus.

The nucleus is the literal brain of operations for the cell. In a tumor a million cells or more are slaved together to operate the cancer as if it was a kind-of special organ who's duty is to continue reproducing more malignant cells on into the future with no end in sight. The limiting element is the availability of enough blood and its associated nutrition to operate the signaling system.

Apoptosis is the principal process of programmed cell death. Technical events that appear during an apoptosis event include characteristic changes that include cell shrinkage, generating heat, hypoxic events and an increase in calcium concentration which causes snappy signaling in the nucleus that triggers and orchestrates the imminent apoptotic event.

Autophagy

Autophagy is from the Greek definition as "self-eating." Inside a living cell's cytoplasm are organelles identified as autophagosomes which move around the cell to sweep up viruses, bacteria and worn out materials from the cell itself. The autophagosomes bag up or concentrates the cell sludge and worn out protein and other debris to be handled by recycling organelles that float in the cytoplasm. Some of the unusable waste is forced out of designated cell ion ports by pumping it through the plasma membrane into the extracellular fluid surrounding the cells. Since some neurons live as long as the body they have to use autophagy to maintain the quality of the overall cell health. Autophagy and mitochondrion can work together to cause apoptosis to trigger programmed cell death to rid the cell of unwanted cell component that can't be rehabilitated. Unlike necrosis, apoptosis produces cell fragments called apoptotic bodies that phagocytic cells are able to engulf, eat, digest and then dispose of in league with the autophagy process in a well-established method to keep the overall cellular system in order.

Pyknosis

The irreversible concentration of chromatin in the nucleus of a cell involved in necrosis or apoptosis. This is followed by condensing its nucleus before expelling it to become a reticulocyte. The maturing neutrophil will be involved in forming blebs that stay in the cell until the end of its life. Blebs are distortion of the nucleus and the cancer cell shape. It is the formation of protrusion or pimple structures of what was previously symmetrical nucleus and over all cell shape. It is followed by fragmentation of the changing nucleus on its way to experiencing karyorrhexis. During bleb formation of the nucleus a sort of pimple formation gives the nucleus an unhealthy appearance, which does not improve.

Karyorrhexis

Karyorrhexis is the ultimate bursting of the cellular nucleus into multiple pieces that cannot be repaired. The nucleus of a cell represents and is equivalent to the brain of any creature, once it is broken into pieces it is finished.

Figure 8:
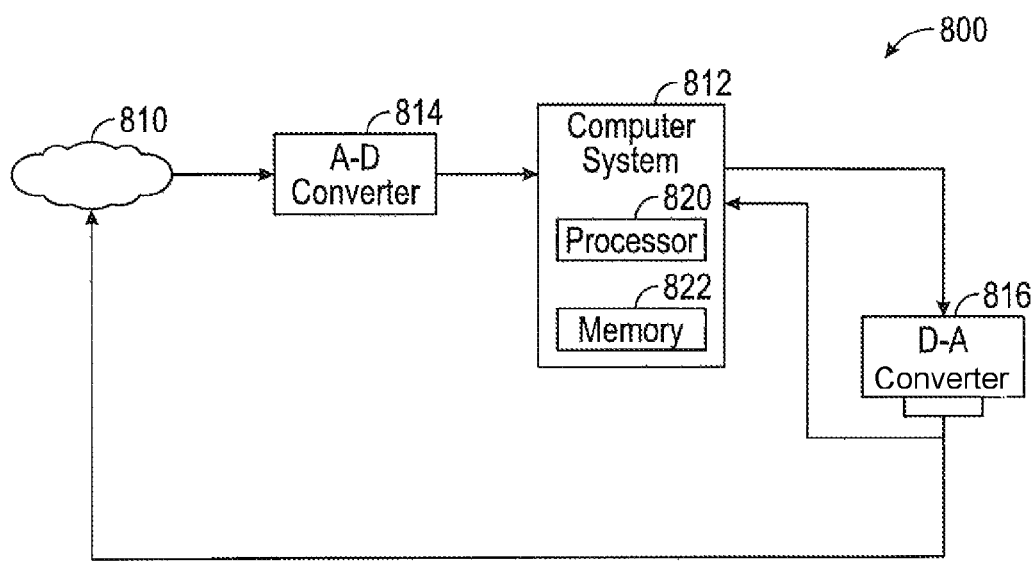
FIGS. 8-9 illustrates a layout of the neuro electric system neuro electric system and example electrodes that can be utilized to pierce the plasma membrane to communicate with the tumor and its cells, in accordance with a preferred embodiment.

Karyorrhexis is an important cancer killing skill which is accomplished by fragmentation of the cancer cell nucleus into apoptotic bodies which are then engulfed and ingested by phagocyte(s). A phagocyte is a special cell that locates and surrounds broken cellular components and then eats them. There are fixed phagocytes that live in the liver, bone marrow and spleen. Such phagocytes are represented by neutrophils and macrophages. Also there are freely moving phagocytes such as leukocytes (white blood cells) that circulate in the blood stream to do their clean-up work. The job of the nucleus is to control all cellular operations and to participate in communication and coordination with nearby cells. If a nucleus is fragmented it is like fragmenting the brain of a human or animal, life cannot go on with such as injury High Speed, Hybrid Scientific Signal Processor to Destroy Cancer Tumor Cell Nuclei A high-speed analog cancer cell unit can be utilized to record cancer cell operational electrical signals and to reprogram such signals before transmitting them back into the malignant cells to trigger apoptosis and karyorrhexis. Such a unit or system is discussed in more detail with respect to the FIG. 8, which illustrates a computer system 812 having at least a processor 820 and a memory 822. A cancer cell cluster or tumor is illustrated at 810 in FIG. 8. By means of an imulus or other probe, such as those shown in FIG. 9, the resident electrical signal or signals of the cancer are then provided to the computer system 812 for storing via memory 822 and processing via processor 822. Typically, the computer system 812 is digital, and in order to accept the electrical signals from the tumor 810, an analog to digital converter 814 can be used. If the computer system 812 employed includes an embedded analog to digital converter, the converter 814 can be omitted.

It is the computer system 812 in which all of the processing, analysis and generation of confounding electrical signals occurs. In order to treat the tumor 810, the confounding electrical signals are applied directly to the tumor 810 via an imulus or probe after conversion to analog state by a digital to analog converter 816.

The technical approach is to initially develop a number of cancer cell resident electrical signals for different species of cancer and perfect reprogrammed confounding type signals. The user then sorts and reprograms the natural signals of the cancer cell and tinkers with the electrical signatures and coding to finally select appropriate treatment electrical signals, also known as confounding electrical signals. This is followed by devising a library/data-base of treatment signals. The collection of treatment signals may be cataloged as to the species of cancer and anatomical location. During treatment of a cancer the first step is to identify the species of cancer and then select the proper confounding signal with which treatment will begin. Once the treatment team knows the species such as carcinoma or sarcoma they select from the computerized library/data-base the most appropriate treatment signal. There are approximately about a total of 200 cancer species in existence. Ultimately the treatment library will be composed of at least as many definitive cancer confounding, interclusio or morifier signals. Carcinoma species is the most common cancer and likely represents something like 50% of all cancerous tumors arising throughout the body.

Once the cancer cell locations in a patient have been identified, the cancer cellular electrical activity has been recorded and analyzed, and an appropriate response has been determined, the medical staff can develop and initiate a treatment protocol. The protocol will follow established medical procedures with the main objective of applying the proper signals and appropriate electrical energy to the cancerous cells to cause apoptosis. The computer system 812 contains a low voltage and amperage power supply to ensure the correct voltage and amperage is delivered to the cancerous cells. The electrical energy delivered is less than 1 volt and less than 10 millionths of an amp for a pulsed application on the cancer over a few seconds. The treatment may be repeated. The range of electrical treatment may span upwards of 2 volts and 70 micro amps and as low as one-tenth of a volt or possibly even lower at 2 microamps or even lower into the picoamp range.

The treatment time may extend, for example, up to 4 minutes or more and may be repeatable over days if required. The treatment signals in the form of an electrical signal will have a definable shape and be encoded to confound the natural electrical activity found in the cancer cell plasma membrane wall and within the very interior of the cell proper. With the use of the proper code to shut off cellular electricity, the result is apoptosis of the cancer. Cancer death can begin in less than an hour once its metabolic processes are shutdown. Cell death actually may occur in less than 10 minutes as a human brain cells do when blood circulation or electrical signals are turned off. Natural resuscitation of the cancer cell may be possible if the confounding electrical signal treatment is too brief or incomplete. Otherwise irreversible biological decay will set in as long as the cellular process has been severely damaged by the treatment signals. The body immune system is expected to consume the dead or dying cancer as soon as the outer cell membrane negative electric charge is off or markedly diminished. It is the strong negative outer electrical charge of the cancer cell membrane glycocalyx that keeps the immune cells from attacking since they too are negatively charged and would be repelled from one another. Normal cells have outer coat charges that are usually positive and are therefore accessible to the negatively charged immune system cells.

Treatment can be accomplished, for example, with a small cable of total diameter no more than a wooden match stick. The imulus or treatment contact unit 918, as shown schematically in FIG. 9, can be implemented in the context of a small device, which in some embodiments may contain up to hundreds or thousands of carbon nanotubes 920. Such nanotubes may be hollow or partitioned. In addition they may be coated with a metal deposition, or chemical that interferes with the glycocalyx strong negative electrical charge. The carbon nanotubes equipped imulus 918 will appear under a microscope like a hairbrush. Each nano fiber tube is about one-ten-thousandths of a human hair in diameter. The imulus 918 can be used to both record and apply the treatment signal and may be of different sizes to fit the various cancer clusters. The physical approach to the cancer can be guided by fluoroscopy or other visualization apparatus or system to insure that the treatment is applied properly and completely and is directed at the correct target.

Figure 9:
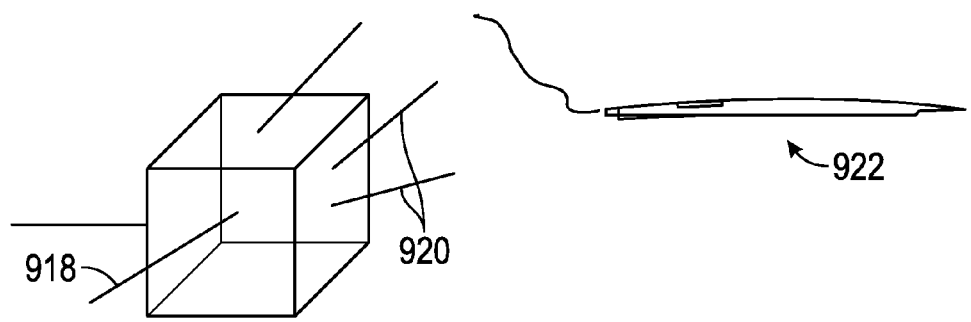

The imulus 918 can be positioned to make contact with the tumor as the primary junction between the computer system 812 and the malignant cellular tumor 810 which is to be treated. Some modified nano carbon tubes may also act like an antenna and only need to be in close proximity of the malignancy to send in the interclusio or impulses mortifier codes. Insertable links, implantable antennas and contact pads or implacable treatment needles of carbon or metal can be in the arsenal of imulus attachments, among others. An alternative imulus 922 is also shown in FIG. 9 with a shape capable of piercing a cancer cell and/or cancer tumor or cluster of cancer cells.

It is preferred that analog computers are used that are as sensitive and able to record the cancer electrical signals as required. As analog computer developments advance they may be more suitable and be the system of choice in destroying cancer cell life. Otherwise the system as illustrated can utilize A-D and D-A converters 814, 816 interfaced with a digital processor in the computer system 12 using appropriate software to control confounding signals.

The main treatment quest can include locating all of the cancer islands and clusters for treatment. Signals to shut down the cancer must affect every malignant cell at a given site. Communication can travel through portions or layers of tumor cells, traveling from cell to cell. Therefore moving the imulus around the tumor 810 may be necessary in some situations to make certain that every cellular communication system present within the malignancy is disabled or destroyed.

While the preferred signal handling system embodiment to destroy cancer cells is a full analog technology, the current state of computer systems may not able to deliver such a scientific computer that would work at the extremely ultra-low voltages and at the speed required to capture and record the natural signals of cancers. Therefore, FIG. 8 outlines an example hybrid system to process cancer treatment codes. Some embodiments can utilize, for example, a hybrid analog/digital computerized system, which requires at its entry an A-D converter 814 of high sensitivity to record the exclusively analog cellular signals of cancers. Secondly, the signal has to be transferred into a digital processor in the computer system 812 where it can be stored and reprogrammed to confound the natural cellular signals and control any power supply required.

The computer system 812 includes several components. First, it should have a typical laptop or desktop computer for control, data acquisition, programming and application of treatment. In some embodiments, however, the computer system 812 may be a mobile device such as, for example, a tablet computing device or a smartphone or another such similar type of hand held device. The computer system can in some situations allow for storage of ambient and environmental signals as well as potentially interfering biological noise so that the treatment or confounding electrical signals can be as pure as possible.

Figure 10:
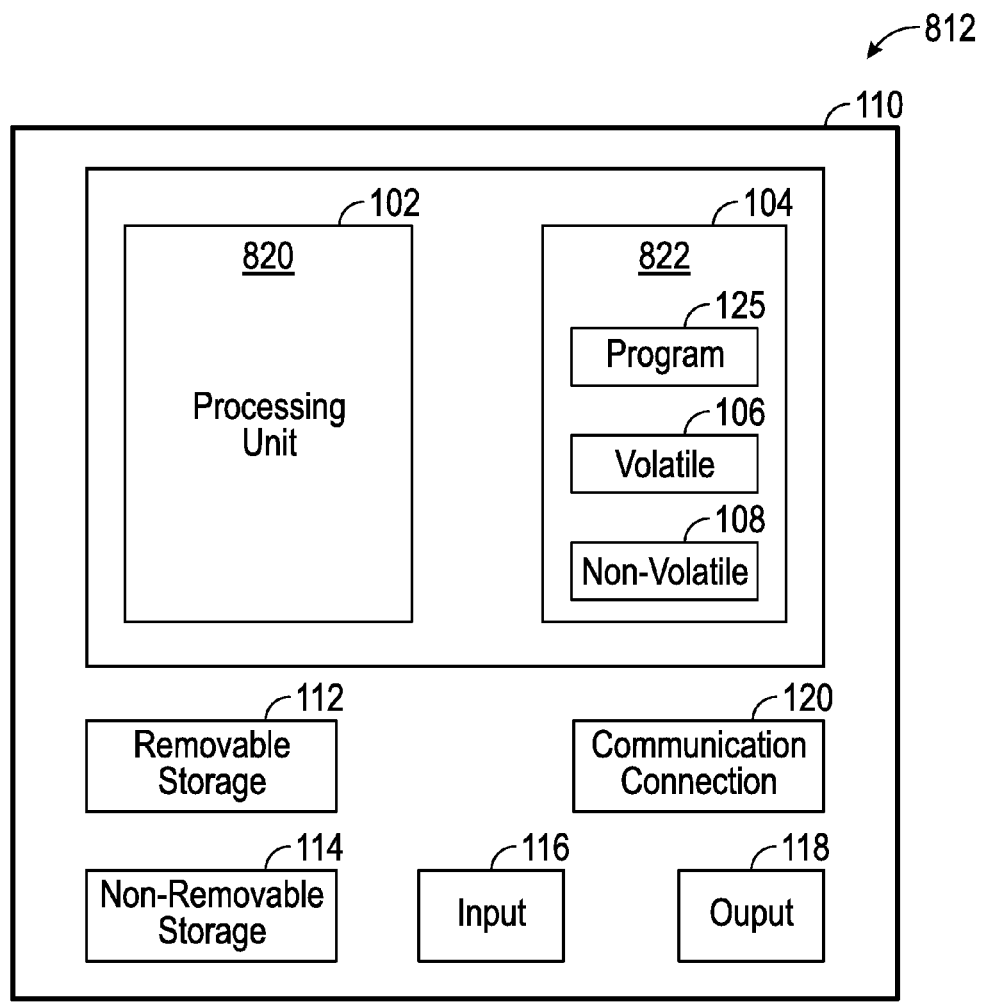
FIG. 10 illustrates a block diagram of a computer system that can be utilized to execute programming for executing the methods, systems, and/or processor-readable media disclosed herein.

FIG. 10 illustrates a block diagram of the computer system 812, which can be utilized to execute programming for executing the methods, systems, and/or processor-readable media disclosed herein. Computer system 812 as shown in FIG. 12 can be implemented as a general computing device in the form of a computer 110, which may include a processing unit 820, memory 820, removable storage 112, and non-removable storage 114. Memory 820 may include, for example volatile memory 106 and non-volatile memory 108. Computer 812 may include or have access to a computing environment that includes—a variety of computer-readable media, such as volatile memory 106 and non-volatile memory 108, removable storage 112 and non-removable storage 114. Computer storage includes, for example, random access memory (RAM), read only memory (ROM), erasable programmable read-only memory (EPROM) and electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage, or other magnetic storage devices, or any other medium capable of storing computer-readable instructions, as well as data, including video frames.

Computer 812 may include or have access to a computing environment that includes input 116, output 118, and a communication connection 120. The computer may operate in a networked environment using a communication connection to connect to one or more remote computers. The remote computer may include a personal computer (PC), server, router, network PC, a peer device or other common network node, or the like. The communication connection may include a Local Area Network (LAN), a Wide Area Network (WAN) or other networks. This functionality is described in more detail in FIG. 23.

Output 118 is most commonly provided as a computer monitor but may include any computer output device. Output 118 allows a user to navigate through the virtual environment embodied by computer system 812. In addition, input 116, which commonly includes a computer keyboard and/or pointing device such as a computer mouse, allows a user to select and instruct computer system 812. A user interface can be provided using output 118 and input 116.

Processor-readable or computer-readable instructions, for example program module 125, are stored on a computer-readable medium and are executable by the processing unit 820 of computer 812. Program module 125 may include an Application. A hard drive, CD-ROM, RAM, Flash Memory, and a USB drive are just some examples of articles including a computer-readable medium.

Figure 11:
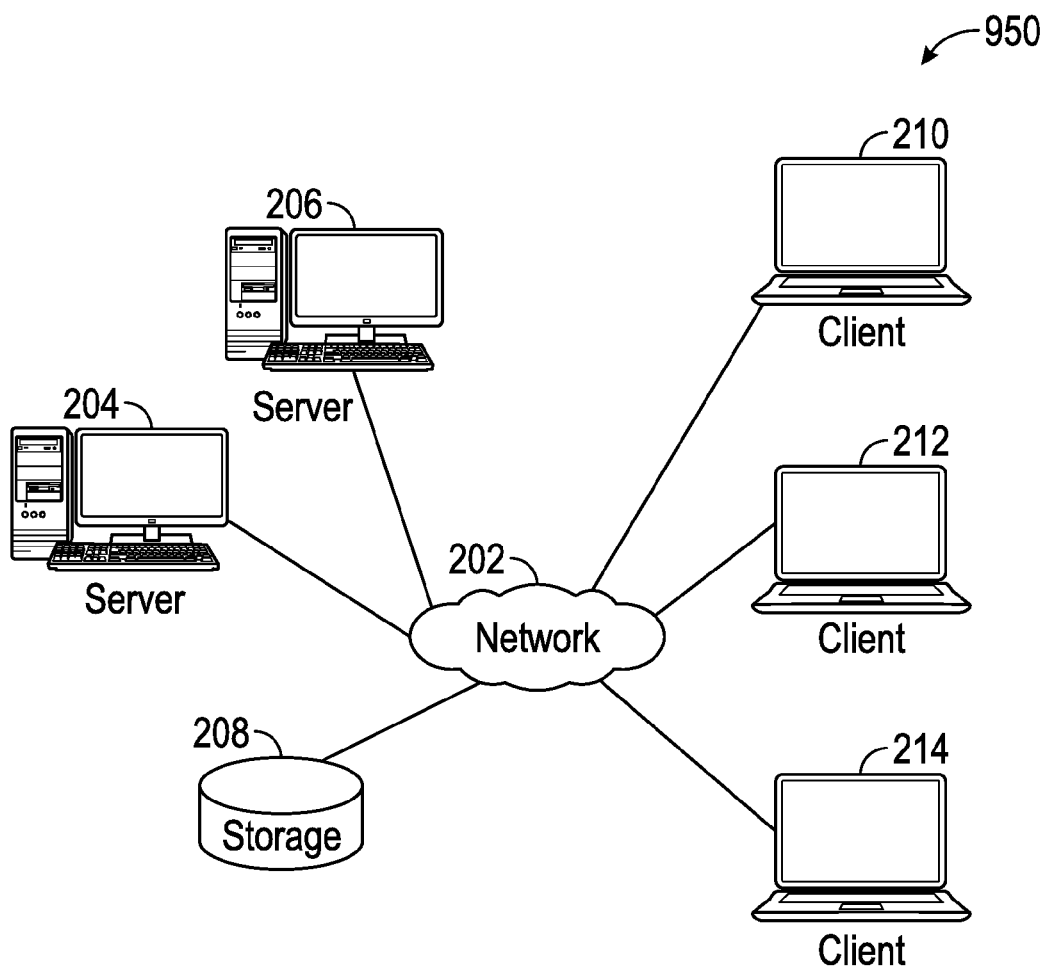
FIG. 11 depicts a graphical representation of a network of data-processing systems in which aspects of the disclosed embodiments may be implemented.

FIG. 11 depicts a graphical representation of a network of data-processing systems 950 in which aspects of the disclosed embodiments may be implemented. Network data-processing system 950 is a network of computers in which embodiments may be implemented. Note that the system 950 can be implemented in the context of a software module such as program module 125. The system 950 includes a network 202 in communication with one or more clients 210, 212, and 214 one of which may be, for example, computer system 812 of FIG. 8. Network 202 is a medium that can be used to provide communications links between various devices and computers connected together within a networked data processing such as computer system 812. Network 202 may include connections, such as wired communication links, wireless communication links, or fiber optic cables. That is, network 202 may be in some embodiments, a wireless communications network (e.g., cellular, Wi-Fi, etc.), and one or more clients such as 210, 212, 214, etc., may be a hand held mobile communications device such as, for example, a smartphone, tablet computing device, etc. Network 202 can further communicate with one or more servers 204 and 206 and a memory storage unit, such as, for example, memory or database 208.

In the depicted example, server 204 and server 206 can connect to network 202 along with storage unit 208. In addition, clients 210, 212, and 214 can connect to network 202. These clients 210, 212, and 214 may be, for example, personal computers or network computers. Computer system 812 depicted in FIG. 11 can be, for example, a client such as client 210, 212, and/or 214. Alternatively, computer system 812 can be implemented as a server, such as servers 204 and/or 206, depending upon design considerations.

In the depicted example, server 204 provides data, such as boot files, operating system images, applications, and application updates to clients 210, 212, and 214. Clients 210, 212, and 214 are clients to server 204 in this example. Network data-processing system 950 may include additional servers, clients, and other devices not shown. Specifically, clients may connect to any member of a network of servers, which provide equivalent content.

In the depicted example, network data-processing system 950 is the internet with network 202 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, government, educational and other computer systems that route data and messages. Of course, network data-processing system 950 also may be implemented as a number of different types of networks, such as for example, an intranet, a local area network (LAN), or a wide area network (WAN). FIG. 11 is intended as an example, and not as an architectural limitation for different embodiments disclosed herein.

The aforementioned description has thus been presented with respect to preferred and alternative embodiments, which can be implemented in the context of a data-processing system such as, for example, computer system 812, in conjunction with program 125, and data-processing system 950 and network 202 depicted in FIGS. 10 and 11. The disclosed embodiments, however, are not limited to any particular application or any particular environment. Instead, those skilled in the art will find that the systems, methods and processor-readable media described herein may be advantageously applied to a variety of system and application software, including database management systems, word processors, and the like. Moreover, the systems, methods and processor-readable media disclosed herein may be embodied on a variety of different platforms including, for example, Macintosh, UNIX, LINUX, and the like. Therefore, the descriptions of the exemplary embodiments, which follow, are for purposes of illustration and not considered a limitation of the disclosed embodiments.

It will be understood that the circuits and other means supported by each block and combinations of blocks can be implemented by special purpose hardware, software or firmware operating on special or general-purpose data processors, or combinations thereof. It should also be noted that, in some alternative implementations, the operations noted in the blocks may occur out of the order noted in the figures. For example, two blocks shown in succession may, in fact, be executed substantially concurrently, or the blocks may sometimes be executed in the reverse order.

The disclosed embodiments thus cover a rapid method to destroy living cancer cells and the tumors they create including metastatic off-spring of such tumor(s), regardless of their location within the human or animal body.

Computer generated analog treatment signal(s) which are aimed at the cellular nucleus are transmitted through the plasma membrane or its ion channel pathways. Signals would travel directly through the phosphor-lipid bilayer and through the internal membrane surface so as to enter the cellular interior. The treatment signals may travel on the intermediate and or microfilaments located in the cancer cellular interior to reach the nucleus.

The treatment signal(s) may reach and influence the nucleus as intended. Such signal(s) are expected to participate in causing apoptosis and karyorrhexis, which leads to the fragmentation and destruction of the nucleus as an operating organelle of the cell. A fractured nucleus would lead to rapid death of the cell, which will be unable to reproduce or communicate with its neighboring cells within the tumor proper.

As a part of the cancer destruction process, calcium can be injected into the process with the nucleus and also to influence the energy source of the cell. That source, referred to as a mitochondrion, is an organelle that floats around in the cytoplasm.

The calcium influences the operational pace of mitochondrion output by converting adenosine diphosphate (ADP) in a resynthesizing process as adenosine tri-phosphate (ATP).

ATP is a kind of bio-fuel for the cell. ATP operates as a cellular fuel to free up chemical energy which is transferred from the ATP to provide the chemical source required for anabolic reactions for cellular processes as it reverts itself back to ADP.

Based on the foregoing, it can be appreciated that a number of embodiments are disclosed herein, preferred and alternative. For example, in one embodiment, a method for destroying cancer cells, can be implemented and can include, for example, the steps or logical operations of inserting calcium ions into a nucleus of at least one cancer cell among a plurality of cancer cells; and fragmenting the nucleus in many cancer cells among the plurality of cancer cells simultaneously with the transmission of destructive analog electrically encoded signals to provide a medical cancer treatment thereof. In another embodiment, a first target of medical cancer treatment is aimed principally into the nucleus and mitochondrion bodies of a malignancy associated with the at least one cancer cell.

In another embodiment, a step or logical operation can be implemented for simultaneously treating thousands or millions of nuclei and mitochondrion cells among the plurality of cancer cells with calcium and neuro encoded analog signals to cause rapid killing of a tumor associated with the malignancy and/or the plurality of cancer cells. In yet another embodiment, an encoded electrical signal burst can be utilized on each malignant solid tumor associated with the at least one cancer cell, regardless of it being within the body or on the surface of a patient thereof, as a part of the medical cancer treatment.

In still another embodiment, a step or logical operation can be implemented for injecting the calcium into, painting the calcium on, pasting the calcium on, and/or spraying the calcium onto a surface of the plurality of cancer cells operating within a tumor, so that the calcium boosts cellular resident operating signals associated with the plurality of cancer cells above their natural electrical excitability and/or metabolic pace throughout. In still another embodiment emplacement of calcium C++ both inside a tumor associated with the at least one cancer cell and on an outer plasma membrane of the at least one cancer cell can be conducted simultaneously. In yet another embodiment, a step or logical operation can be provided for over-wrapping a tumor associated the at least one cancer cell among the plurality of cancer cells with a waterproof material if the tumor is situated in a location accessible to the over-wrapping. In still another embodiment, a step or logical operation can be provided for maintaining the waterproof material on the tumor for a particular period of time or such time as a physician deems appropriate.

In yet another embodiment, a step or logical operation can be provided for smothering a tumor associated with the at least one cancer cell from a calcium saturated wrap to deny access to extra cellular solute concentration around the at least one cancer cell or the tumor associated with the at least one cancer cell to inhibit a transport of solutes and ions and water to cause the at least one cancer cell to suffer osmotic shock causing swelling and either to burst or undergo apoptosis. In still another embodiment, a high-speed hybrid system such as system 800 shown in FIG. 8 can be employed to record from varying types of electrodes, signals associated with the at least one cancer cell to process the signals to produce the destructive analog electrically encoded signals. In another embodiment, one or more electrodes among the varying types of electrodes can be capable of piercing a plasma membrane associated with the at least one cancer cell. In yet another embodiment, at least one electrode among the varying types of electrodes can be provided as, for example, a pipette electrode or a patch-clamp hollow glass electrode with saline solution electrodes so as to enter calcium, potassium or sodium ion ports of the at least one cancer cell to record the signals associated with the at least one cancer cell.

In another embodiment, a system for destroying cancer cells, can be implemented. Such a system can include, for example, a processor and/or a memory; a device for inserting calcium ions into a nucleus of at least one cancer cell among a plurality of cancer cells; and wherein the nucleus is fragmented in many cancer cells among the plurality of cancer cells simultaneously with the transmission of destructive analog electrically encoded signals processed by the processor and/or retrieved from the memory to provide a medical cancer treatment thereof.

It will be appreciated that variations of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art, which are also intended to be encompassed by the following claims.

What is claimed is:

1. A method for destroying cancer cells, said method comprising:
   inserting calcium ions into a nucleus of at least one cancer cell among a plurality of cancer cells; and
   transmitting to said nucleus destructive analog electrically encoded signals that lead to the fragmentation and destruction of said nucleus of said at least one cancer cell among said plurality of cancer cells to provide a medical cancer treatment thereof, wherein a first target of said medical cancer treatment is aimed principally into said nucleus and mitochondrion bodies of a malignancy associated with said at least one cancer cell.

2. The method of claim 1 further comprising simultaneously treating thousands or millions of nuclei and mitochondrion cells among said plurality of cancer cells with calcium and neuro encoded analog signals to cause rapid killing of a tumor associated with said plurality of cancer cells.

3. The method of claim 1 further comprising an encoded electrical signal burst that is utilized on each malignant solid tumor associated with said at least one cancer cell, regardless of said each malignant solid tumor being within a body or on a surface of a patient thereof, as a part of said medical cancer treatment.

4. The method of claim 1 further comprising injecting said calcium into, painting said calcium on, pasting said calcium on, and/or spraying said calcium onto a surface of said plurality of cancer cells operating within a tumor, so that said calcium boosts cellular resident operating signals associated with said plurality of cancer cells above their natural electrical excitability and/or metabolic pace throughout.

5. The method of claim 1 wherein emplacement of calcium C++ both inside a tumor associated with said at least one cancer cell and on an outer plasma membrane of said at least one cancer cell is conducted simultaneously.

6. The method of claim 1 further comprising over-wrapping a tumor associated with said at least one cancer cell among said plurality of cancer cells with a waterproof material if said tumor is situated in a location accessible to said over-wrapping.

7. The method of claim 6 further comprising maintaining said waterproof material on said tumor for a particular period of time or such time as a physician deems appropriate.

8. The method of claim 1 further comprising smothering a tumor associated with said at least one cancer cell from a calcium saturated wrap to deny access to extra cellular solute concentration around said at least one cancer cell or said tumor associated with said at least one cancer cell to inhibit a transport of solutes and ions and water to cause said at least one cancer cell to suffer osmotic shock causing swelling and either to burst or undergo apoptosis.

9. The method of claim 1 further comprising utilizing a high-speed hybrid system to record from varying types of electrodes, signals associated with said at least one cancer cell to process said signals to produce said destructive analog electrically encoded signals.

10. The method of claim 9 wherein at least one electrode among said varying types of electrodes is capable of piercing a plasma membrane associated with said at least one cancer cell.

11. The method of claim 9 wherein at least one electrode among said varying types of electrodes comprises a pipette electrode or patch-clamp hollow glass electrode with saline solution electrodes so as to enter calcium, potassium or sodium ion ports of said at least one cancer cell to record said signals associated with said at least one cancer cell.

12. The method of claim 1 wherein said destructive analog electrically encoded signals cause at least one of necrosis, apoptosis, karyolysis, pyknosis, and karyorrhexis in said at least one cancer cell among said plurality of cancer cells.

13. A system for destroying cancer cells, said system comprising:
a processor and a memory;
a device for inserting calcium ions into a nucleus of at least one cancer cell among a plurality of cancer cells; and
wherein destructive analog electrically encoded signals processed by said processor and retrieved from said memory to provide a medical cancer treatment thereof are transmitted to said nucleus leading to the fragmentation and destruction of said nucleus of said at least one cancer cell among said plurality of cancer cells, wherein a first target of medical cancer treatment is aimed principally into said nucleus and mitochondrion bodies of a malignancy associated with said at least one cancer cell.

14. The system of claim 13 wherein thousands or millions of nuclei and mitochondrion cells among said plurality of cancer cells are simultaneously treated with calcium and neuro encoded analog signals to cause rapid killing of a tumor associated with said plurality of cancer cells and wherein an encoded electrical signal burst is utilized on each malignant solid tumor associated with said at least one cancer cell, regardless of each said malignant solid tumor being within the body or on the surface of a patient thereof, as a part of said medical cancer treatment.

15. The system of claim 13 wherein said calcium is injected into, painted on, pasted on, and/or sprayed onto a surface of said plurality of cancer cells operating within a tumor, so that said calcium boosts cellular resident operating signals associated with said plurality of cancer cells above their natural electrical excitability and/or metabolic pace throughout.

16. The system of claim 13 wherein emplacement of calcium C++ both inside a tumor associated with said at least one cancer cell and on an outer plasma membrane of said at least one cancer cell is conducted simultaneously.

17. The system of claim 13 wherein a tumor associated with said at least one cancer cell among said plurality of cancer cells is over-wrapped with a waterproof material if said tumor is situated in location accessible to over-wrapping and wherein said waterproof material is maintained on said tumor for a particular period of time or such time as a physician deems appropriate.

18. The system of claim 13 further comprising a calcium saturated wrap, wherein a tumor associated with said at least one cancer cell is smothered with said calcium saturated wrap to deny access to extra cellular solute concentration around said at least one cancer cell or said tumor associated with said at least one cancer cell to inhibit a transport of solutes and ions and water to cause said at least one cancer cell to suffer osmotic shock causing swelling and either to burst or undergo apoptosis.

19. The system of claim 13 further comprising a high-speed hybrid system comprising said processor and said memory to record from varying types of electrodes, signals associated with said at least one cancer cell to process said signals to produce said destructive analog electrically encoded signals.

20. The system of claim 13 wherein said destructive analog electrically encoded signals cause at least one of necrosis, apoptosis, karyolysis, pyknosis, and karyorrhexis in said at least one cancer cell among said plurality of cancer cells.

* * * * *